(12) United States Patent
Trader et al.

(10) Patent No.: US 11,092,596 B2
(45) Date of Patent: Aug. 17, 2021

(54) MATERIAL AND METHOD TO SCREEN PROTEASOME STIMULATORS

(71) Applicant: Purdue Research Foundation, West Lafayette, IN (US)

(72) Inventors: Darci Jones Trader, West Lafayett, IN (US); Rachel Anne Coleman, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 76 days.

(21) Appl. No.: 16/128,697

(22) Filed: Sep. 12, 2018

(65) Prior Publication Data

US 2019/0086398 A1    Mar. 21, 2019

Related U.S. Application Data

(60) Provisional application No. 62/559,076, filed on Sep. 15, 2017.

(51) Int. Cl.
| | |
|---|---|
| *C07K 7/08* | (2006.01) |
| *G01N 33/542* | (2006.01) |
| *G01N 33/68* | (2006.01) |
| *G01N 33/573* | (2006.01) |

(52) U.S. Cl.
CPC ............. *G01N 33/542* (2013.01); *C07K 7/08* (2013.01); *G01N 33/573* (2013.01); *G01N 33/6848* (2013.01); *G01N 2333/4706* (2013.01); *G01N 2333/9643* (2013.01); *G01N 2800/2835* (2013.01)

(58) Field of Classification Search
None
See application file for complete search history.

(56) References Cited

PUBLICATIONS

Huang, X., et al., "An atomic structure of the human 26S proteasome", Nature Structural & Molecular Biology, 23, pp. 778-785, 2016.
Trader, D., et al., "A Reversible and Highly Selective Inhibitor of the Proteasomal Ubiquitin Receptor Rpn13 Is Toxic to Multiple Myeloma Cells", JACS, pp. 6312-6319, 2015.
Kapetanou, M., et al., "Proteasome activation enhances stemness and lifespan of human mesenchymal stem cells", Elsevier, pp. 226-235, 2017.
Latham, M., et al., "Understanding the mechanism of proteasome 20S core particle gating" PNAS, 111, pp. 5532-5537, 2014.
Huang, L, et al., "Activation and inhibition of the proteasome by betulinic acid and its derivatives", FEBS Letters, 581, pp. 4955-4959, 2007.
Priestman, M., et al., "Multicolor Monitoring of the Proteasome's Catalytic Signature", ACS Chem Biol., 10, pp. 433-440, 2015.
Leestemaker, Y., et al., "Proteasome Activation by Small Molecules", Cell Chemical Biology, 24, pp. 725-736, 2017.
Keita, M., et al, "F NMR monitoring of the eukaryotic 20S proteasome chymotrypsin-like activity: an investigative tool for studying allosteric regulation", Org., Biomol., Chem., 12. pp. 4576-4581, 2014.
Bruin, G. et al., "A Set of Activity-Based Probes to Visualize Human (Immuno) proteasome Activities", Angew., Chem. Int. Ed., 55, pp. 4199-4203, 2016.
Trader, D., et al., "Establishment of a suite of assays that support the discovery of proteasome stimulators", Biochimica et Biophysica Acta, 1861, pp. 892-899, 2017.
Lee , B., et al., "Enhancement of proteasome activity by a small-molecule inhibitor of USP14", Nature, 467, pp. 179-184, 2010.
Chen, L., et al., "Enhanced Degradation of Misfolded Proteins Promotes Tumorigenesis", Cell Reports, 18, pp. 3143-3154, 2017.
Liu, C., et al., "Endoproteolytic Activity of the Proteasome" Science, 299, pp. 408-411, 2003.
Singla, P., et. al., "Triazine as a promising scaffold for its versatile biological behavior", Elsevier, 102, pp. 39-57, 2015.

*Primary Examiner* — Thomas S Heard
(74) *Attorney, Agent, or Firm* — Purdue Research Foundation; Liang Zeng Yan

(57) ABSTRACT

A group of peptide compounds and their use in identifying molecules that stimulate proteasome or immunoproteasome are disclosed herein.

3 Claims, 19 Drawing Sheets

Specification includes a Sequence Listing.

FIG. 2A
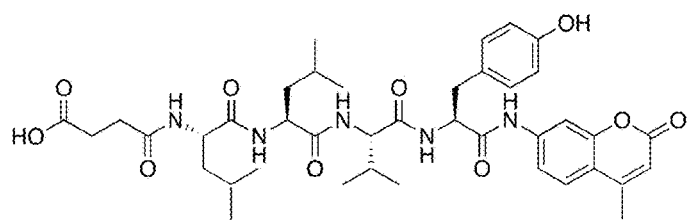
FIG. 2B
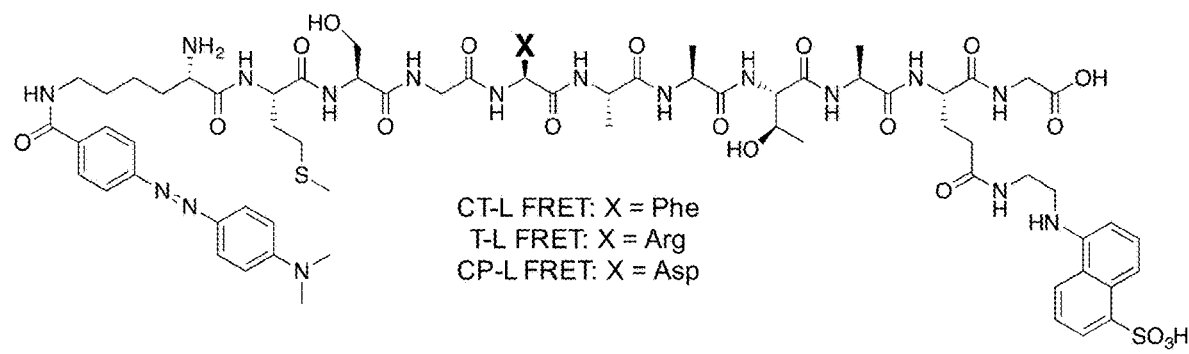
CT-L FRET: X = Phe
T-L FRET: X = Arg
CP-L FRET: X = Asp
FIGURE 2

FIG. 3A
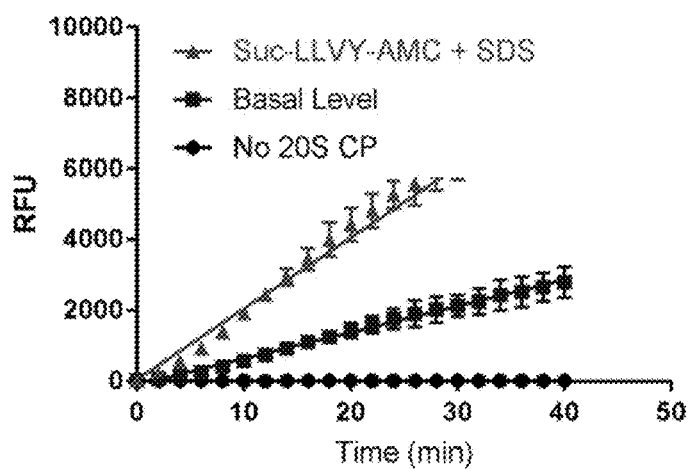
FIG. 3B
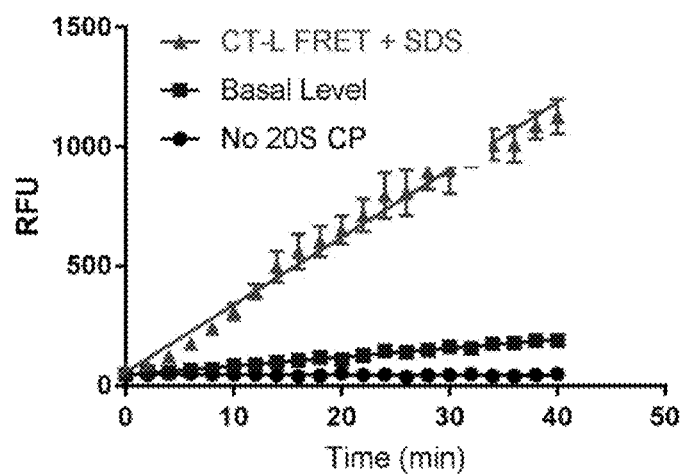
FIG. 3C
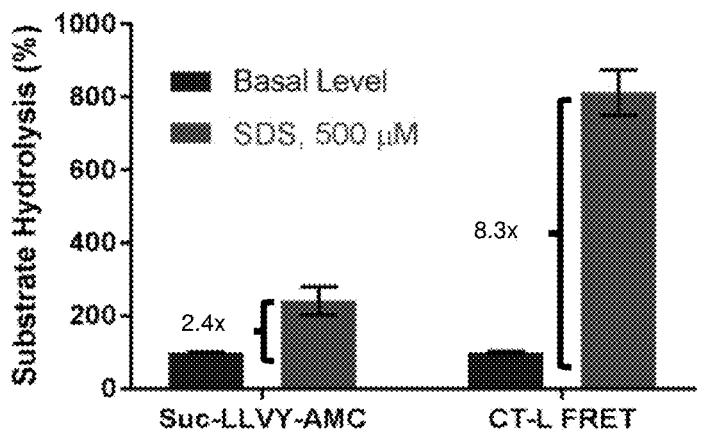
FIGURE 3

FIG. 4A
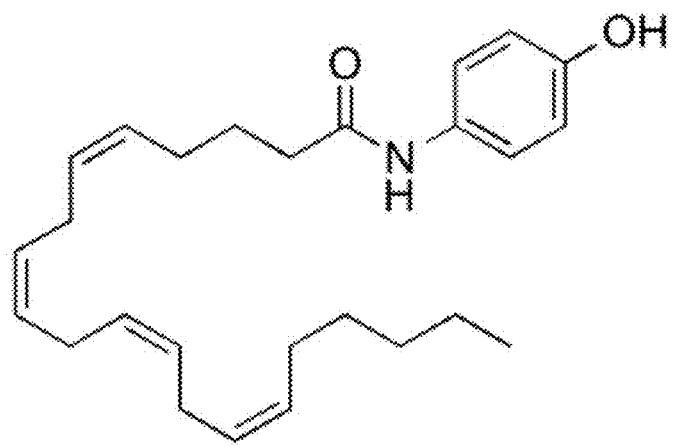
FIG. 4B
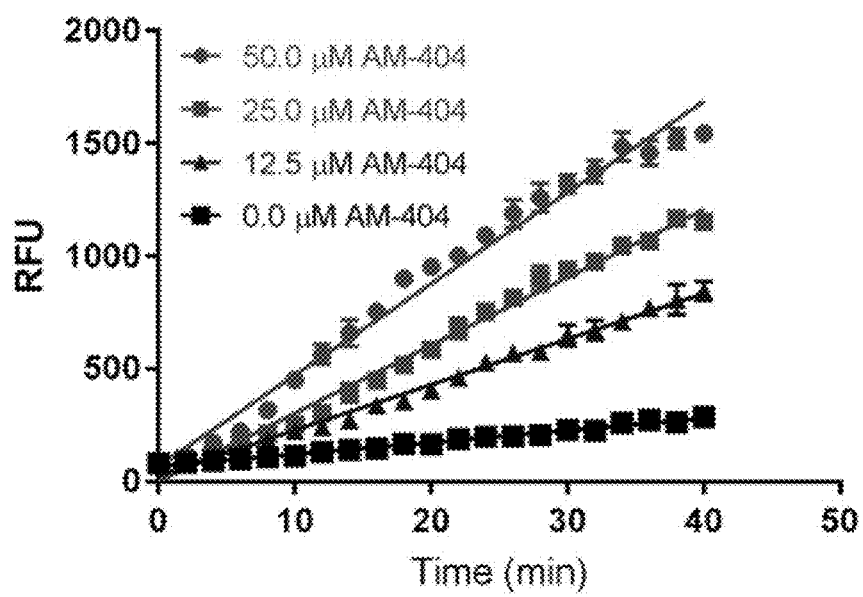
FIGURE 4

FIG. 6A
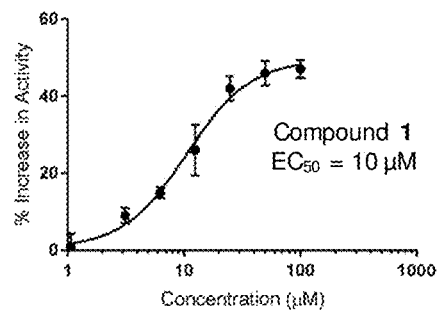
FIG. 6B
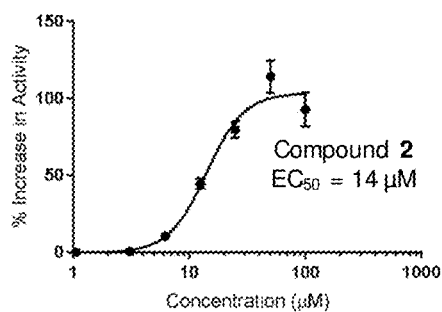
FIG. 6C
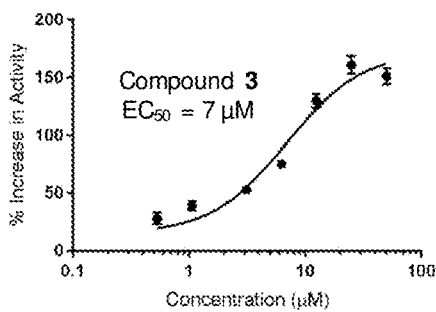
FIGURE 6

FIG. 7A
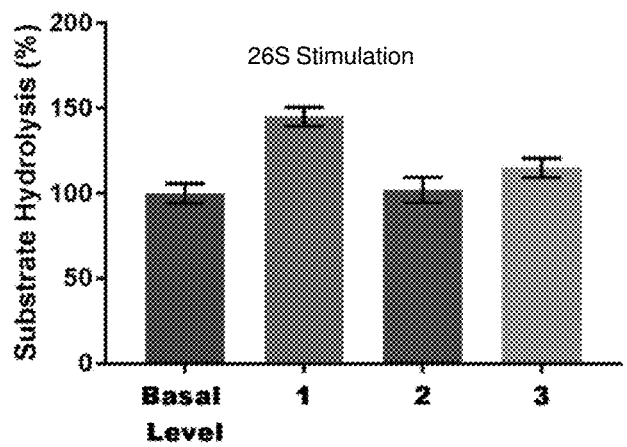
FIG. 7B
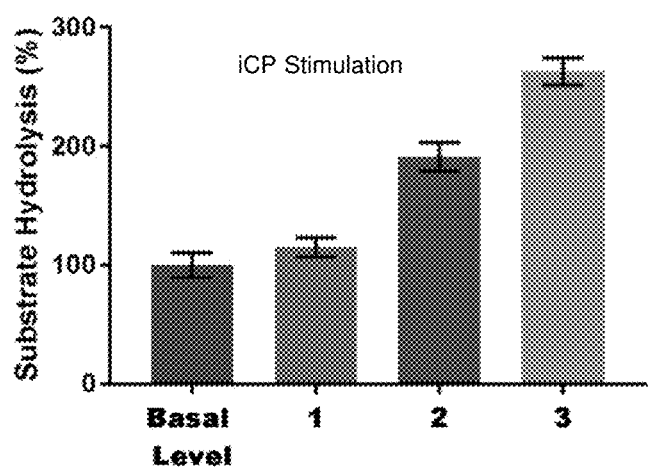
FIGURE 7

FIG. 11A
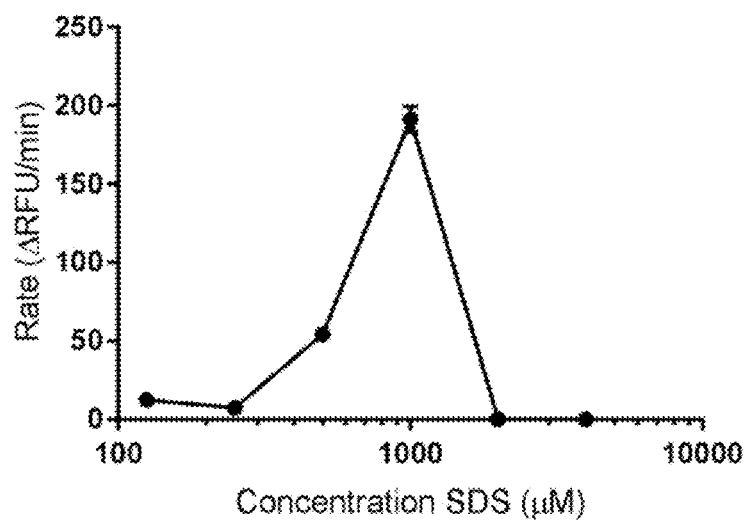
FIG. 11B
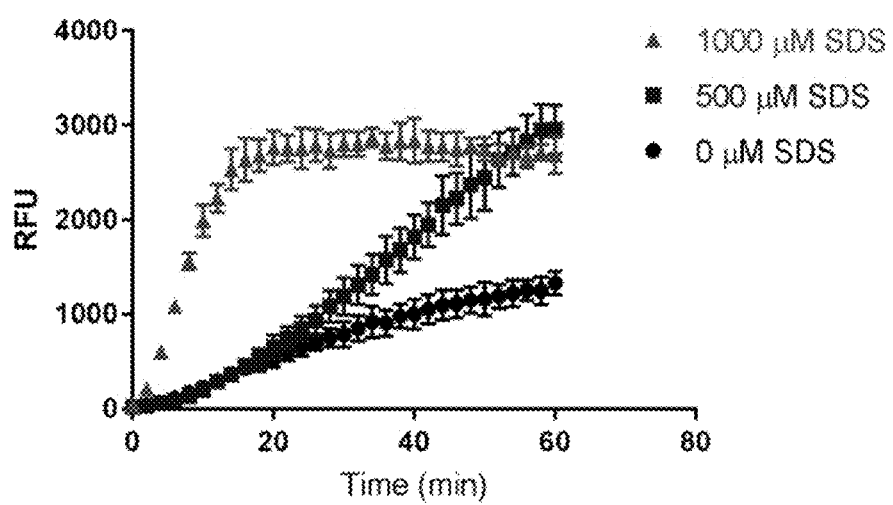
Figure 11

FIG. 12A
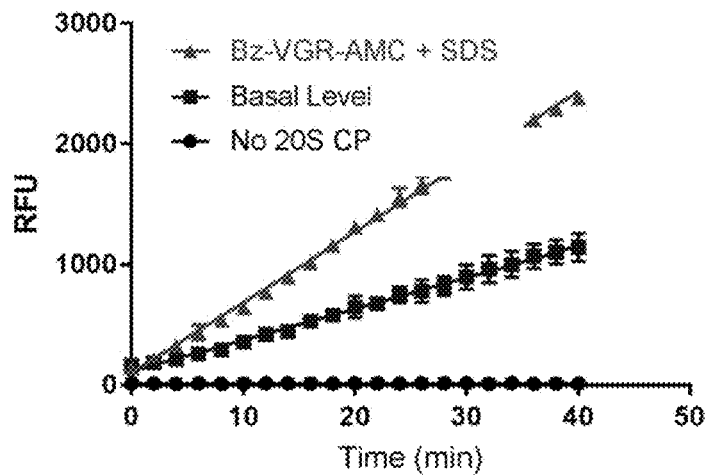
FIG. 12B
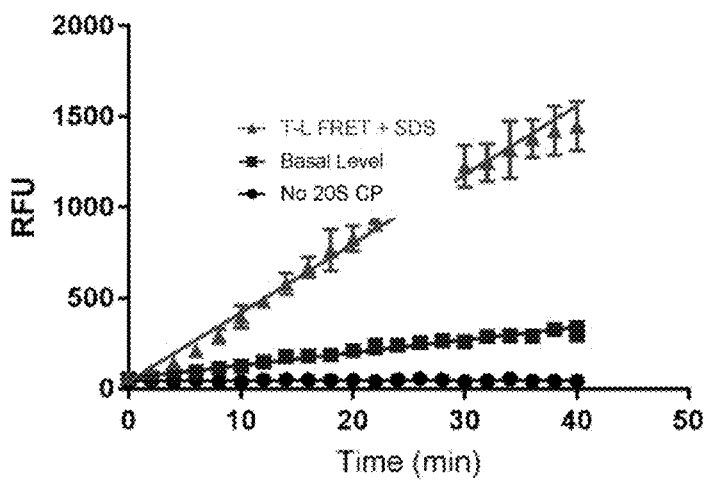
FIG. 12C
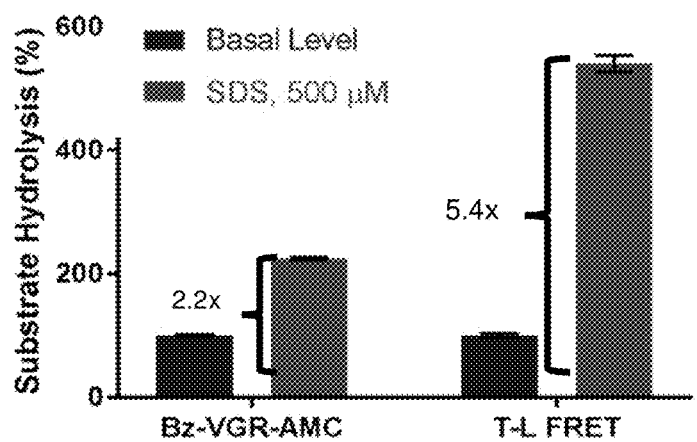
Figure 12

FIG. 13A
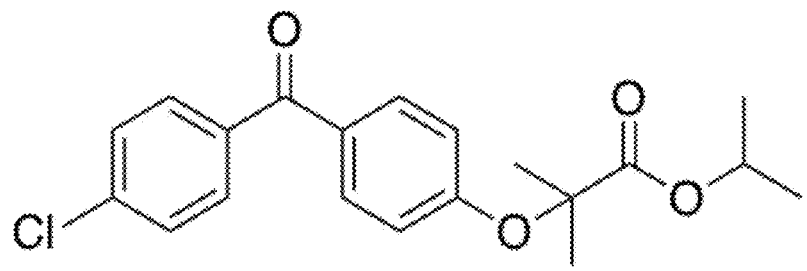
FIG. 13B
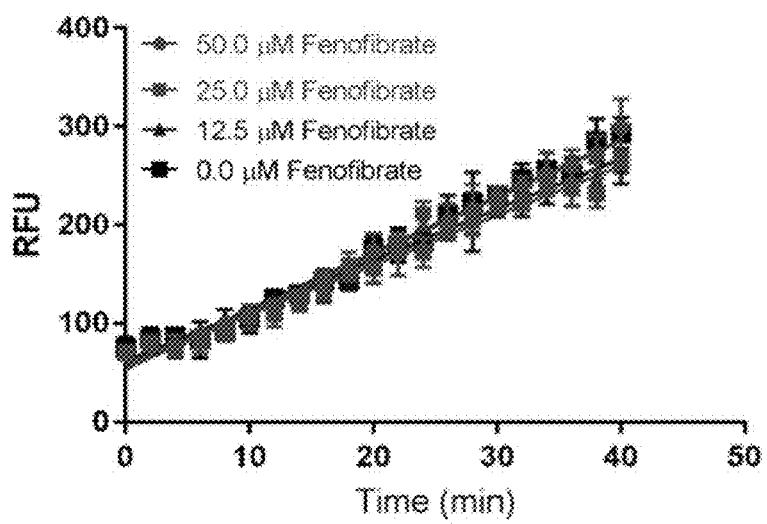
Figure 13

FIG. 15A
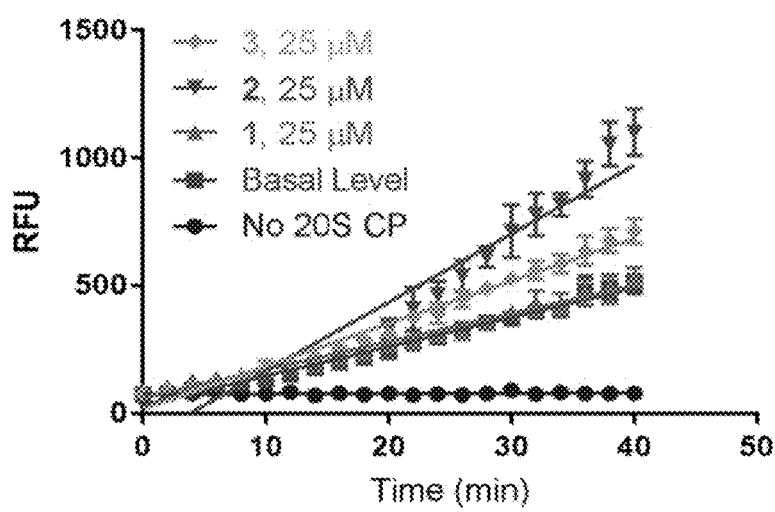
FIG. 15B
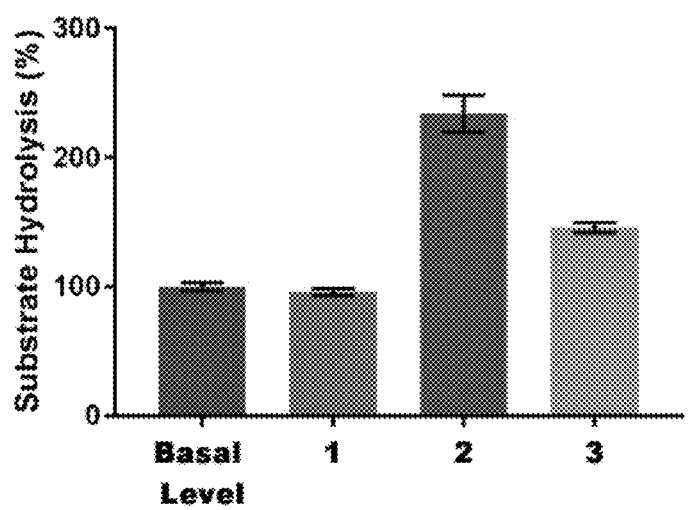
Figure 15

FIG. 17A
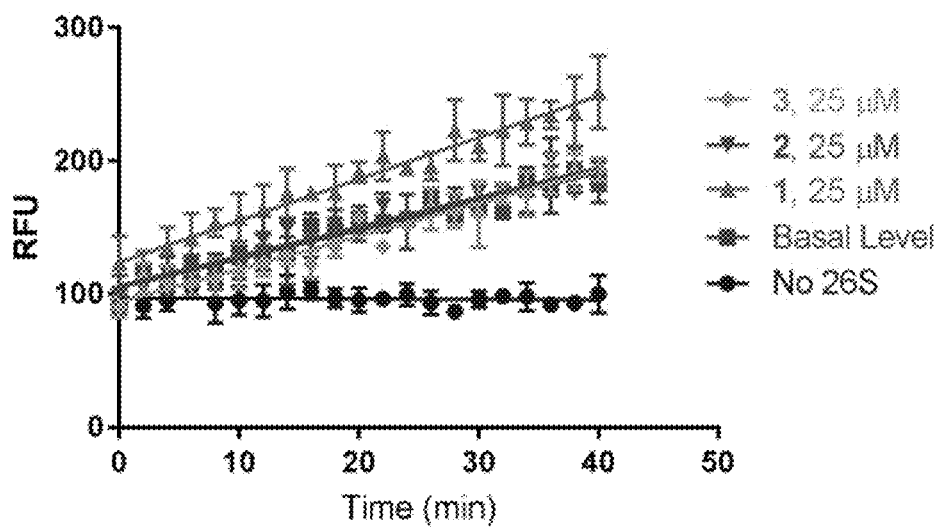
FIG. 17B
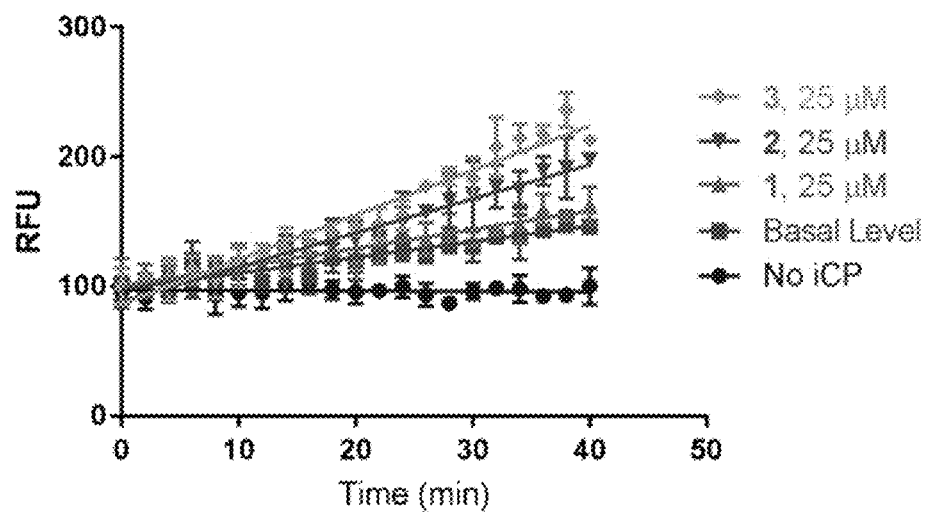
Figure 17

Figure 18:
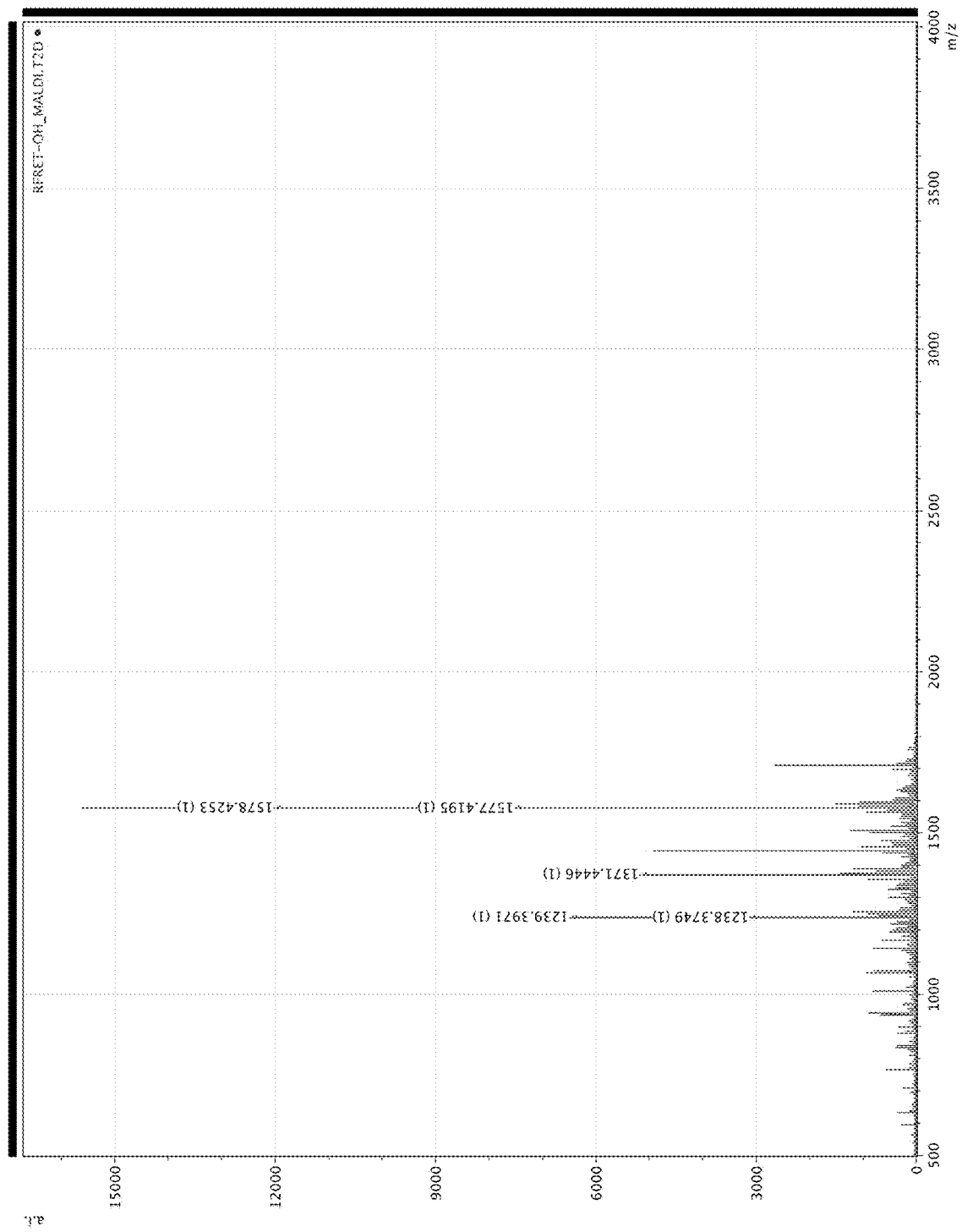

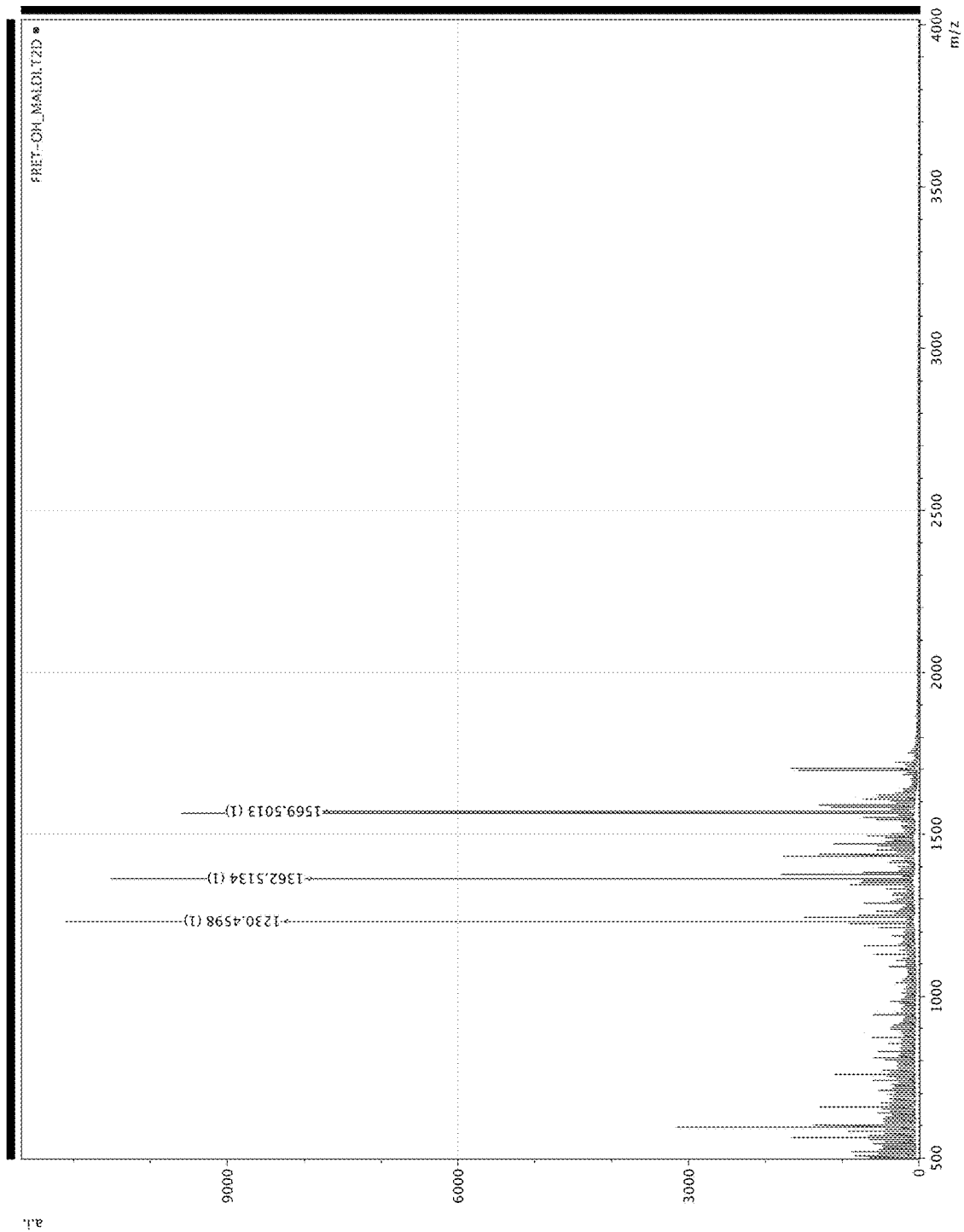
Figure 18 (Contd.)

MATERIAL AND METHOD TO SCREEN PROTEASOME STIMULATORS

CROSS REFERENCE TO RELATED APPLICATION

This present patent application relates to and claims the priority under 35 U.S.C. § 119(e) to U.S. Provisional Patent Application Ser. No. 62/559,076 filed on Sep. 15, 2017, the content of which is hereby incorporated by reference in its entirety into the present disclosure.

STATEMENT OF SEQUENCE LISTING

A computer-readable form (CRF) of the Sequence Listing is submitted with this application. The file, entitled 67888-02_Seq_Listing_ST25_txt, is generated on Sep. 29, 2020. Applicant states that the content of the computer-readable form is the same and the information recorded in computer readable form is identical to the written sequence listing.

FIELD OF INVENTION

This disclosure relates to a fluorescent probe that helps identifying molecules that stimulate proteasome or immunoproteasome. Particularly, a group of FRET-reporter peptides are used to identify at least two modes of action of stimulating proteasome core particle 20S CP to degrade proteins, including gate opener and chymotrypsin-like activity of 20S CP.

BACKGROUND

One of the most basic, essential cellular processes is the degradation of proteins. This is performed through two main pathways. Proteins can be shuttled to the lysosome or degraded by a large enzyme complex known as the proteasome.[1] The 26S proteasome is composed of the 19S regulatory particle (19S RP) and the 20S core particle (20S CP), FIG. 1.[2] For a protein to be degraded by the 26S proteasome, it needs to be tagged with ubiquitin. This tag is then recognized by a subunit of the 19S regulatory particle, and upon this recognition, the 19S RP recruits deubiquitinases to remove the ubiquitin, unwinds the protein to limit its tertiary structure, and then shuttles it into the 20S CP. The 19S RP is also responsible for directly interacting with the N-termini of the α-rings of the 20S CP to open the pore or gate to allow protein substrates to enter.[3] It is the responsibility of the 20S CP to hydrolyze the protein into peptides that can then be recycled to make new proteins or used as antigenic peptides. The 20S CP has the ability to cleave proteins into peptides with chymotrypsin-, trypsin- and caspase-like activity.

The 26S proteasome has been previously validated as a therapeutic target. A number of small molecules have been developed that behave as proteasome inhibitors and lead to cytotoxicity in cancers.[4] The most well-known is bortezomib (Velcade C), which is a covalent inhibitor that interacts with the chymotrypsin-like site on the 20S CP to prevent protein hydrolysis and is prescribed for patients with refractory multiple myeloma. Recently, there have also been reports of inhibitors to subunits that compose the 19S RP; however, none have made it into the clinic yet.[5,6]

Hydrolysis of proteins is an essential process for all cell types, and disruption of the activity of the proteasome, either the 26S or 20S isoform, can lead to cell death. Unfortunately, as cells age or are affected by protein accumulation diseases such as Parkinson's, the level of proteins that assemble to form the 19S RP is greatly diminished as compared to younger or healthy cells.[7] Without the 19S RP, ubiquitin-dependent protein degradation cannot occur, but the 20S CP can degrade proteins, slowly, in an ubiquitin-independent manner.[8] The levels of the proteins that compose the 20S CP remain the same between diseased and healthy cells.[9] When the 20S CP is not capped by the 19S RP, only small, intrinsically disordered proteins can be degraded, but only at a slow rate.

There has long been a general hypothesis that if one could increase the rate at which the 20S CP can turn over proteins, this could alleviate the negative effects associated with protein accumulation diseases.[10-12] It is believed that this can be done through two mechanisms with small molecules. The first is stimulating the gate of the 20S CP to open, allowing more substrates to enter at a faster rate.[13-14] The second mechanism is through an allosteric interaction with one of the active sites.[15]

There have been previous reports of peptides and small molecules that can stimulate the 20S CP. For example, peptides that mimic the C-terminus of some of the 19S RP's ATPases have been described to stimulate the 20S CP.[16-18] There have also been natural products reported to behave as 20S CP stimulation agents, including oleuropein, a major component of olive oil, and betulinic acid, a natural product originally discovered from the white birch tree.[19-21] The aforementioned molecules were discovered by utilizing a small reporter peptide, composed of 3-4 amino acids plus a terminal aminomethyl coumarin group, FIG. 2A. Upon interaction with the 20S CP, the amino methyl coumarin group is hydrolyzed from the peptide, and a fluorescent signal begins to accumulate. For this to be a therapeutic route of interest, the 20S CP must be stimulated to turn over a protein, and therefore, screening with such a small reporter peptide could yield results that are not biologically relevant. Additionally, because of the small size of the reporter, it can easily diffuse into the 20S CP and be turned over with no stimulation. Performing a high throughput screen with a reporter this small will have a significant number of false negatives because of the high basal level of activity of the 20S CP, making the detection of weak 20S CP stimulators a challenge, especially those that are allosteric stimulators.

There is a need to provide a more accurate reporter peptide that can identify stimulators of 20S CP.

SUMMARY OF THE INVENTION

This disclosure provides a fluorescent reporter for identifying core protein (CP) 20S stimulators. The fluorescent reporter comprising the structure of Lys(Y1)-Met-Ser-Gly-X-Ala-Ala-Thr-Ala-Glu(Y2)-Gly, wherein X is selected from the group consisting of Phe (SEQ ID NO: 1), Arg (SEQ ID NO: 2) and Asp (SEQ ID NO: 3);

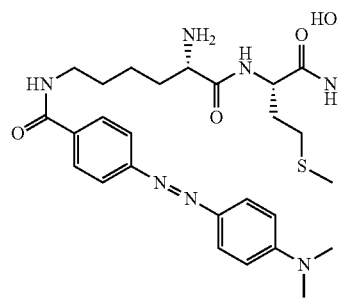 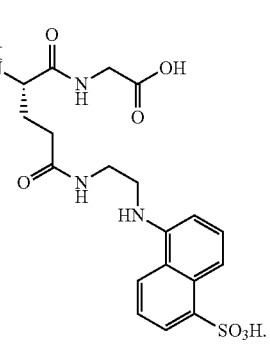

CT-L FRET: X = Phe
T-L FRET: X = Arg
CP-L FRET: X = Asp

This disclosure provides a group of compounds that stimulates CP 20S. The compounds have the structure named 1, 2 and 3. Among these compounds, compounds 2-3 provides gate opening function for 20S CP and compound 1 provides allosteric interaction with beta-5 subunit of 20S CP, which stimulates chymotrypsin-like activity.

This disclosure further provides a method to identify a potent CP 20S stimulator to accelerate protein degradation. The method comprising:

providing a fluorescence reporter with the following structure:
Lys(Y1)-Met-Ser-Gly-X-Ala-Ala-Thr-Ala-Glu(Y2)-Gly, wherein X is selected from the group consisting of Phe (SEQ ID NO: 1), Arg (SEQ ID NO: 2) and Asp (SEQ ID NO: 3);

Individually pairing the fluorescence reporter with each candidate compound in a library and supplying CP 20S to the pair to obtain the fluorescence reporter hydrolysis reading;

providing a positive control with the fluorescence reporter and CP 20S stimulator to obtain a reference fluorescence reporter hydrolysis reading;

Comparing each candidate compound associated fluorescence reporter reading with the reference fluorescence reporter hydrolysis reading; and Identifying the compound that matches or surpasses the reference fluorescence reporter hydrolysis reading as a hit compound stimulator to CP 20S.

In some preferred embodiment, the aforementioned positive control is sodium dodecyl sulfate (SDS) or AM-404.

In some preferred embodiment, the aforementioned fluorescence reporter hydrolysis reading is expressed by the rate of hydrolysis in relative fluorescence units (RFU) per minute (ΔRFU/Min).

This disclosure further provides a method of treating a protein accumulation related disease in a patient. The method comprising:

using a fluorescent reporter to identify at least one 20S CP stimulator;

applying pharmaceutically effective amount of said at least one 20S CP stimulator to the patient.

In some preferred embodiment, the aforementioned fluorescent reporter is Lys(Y1)-Met-Ser-Gly-X-Ala-Ala-Thr-Ala-Glu(Y2)-Gly, wherein X is selected from the group consisting of Phe (SEQ ID NO: 1), Arg (SEQ ID NO: 2) and Asp (SEQ ID NO: 3);

In some preferred embodiment, the aforementioned disease is Parkinson's disease and the protein accumulated is α-synuclein.

These and other features, aspects and advantages of the present invention will become better understood with reference to the following figures, associated descriptions and claims.

BRIEF DESCRIPTION OF THE DRAWINGS AND TABLES

Figure 1:
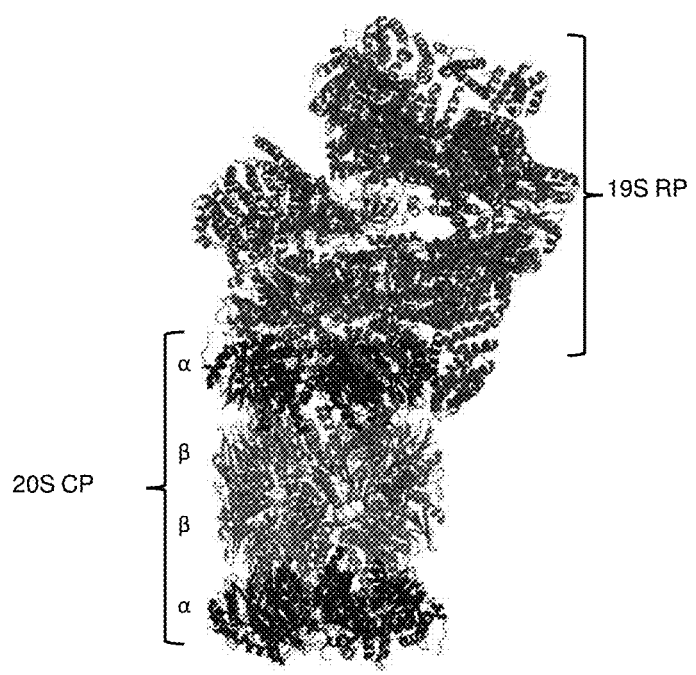

FIG. 1. The proteasome can degrade proteins through a ubiquitin-dependent process when the 19S RP and 20S CP associate to form the 26S proteasome. The 20S CP can degrade proteins but can only accept small, intrinsically disordered proteins and does so at a slow rate.

FIG. 2. (FIG. 2A) Typically used reporter peptide to monitor the chymotrypsin-like activity of the 20S CP (SEQ ID NO: 4). (FIG. 2B) To more efficiently detect 20S CP stimulation molecules, we developed a series of FRET probes to monitor the variety of 20S CP activities, wherein CT-L FRET, X=Phe (SEQ ID NO: 1); T-L FRET, X=Arg (SEQ ID NO: 2); and CP-L FRET, X=Asp (SEQ ID NO: 3).

FIG. 3. Accumulation of fluorescence upon the cleavage of the amino coumarin group (FIG. 3A) or the CT-L FRET (FIG. 3B) reporter by the 20S CP with and without SDS. (FIG. 3C) Direct comparison of the basal level of 20S CP activity to that when SDS is added with the four-amino acid reporter or the CT-L FRET. The rate of hydrolysis of the larger FRET reporter increases more in the presence of a stimulator than the four-amino acid reporter.

FIG. 4. (FIG. 4A) Chemical structure of AM-404. (FIG. 4B) Increase in fluorescence intensity in the presence of AM-404 is dose-dependent. The concentrations of AM-404 had the following increases in the rate of hydrolysis: 50.0 μM, 7-fold increase; 25.0 μM, 5-fold increase; 12.5 μM, 4-fold increase.

Figure 5:
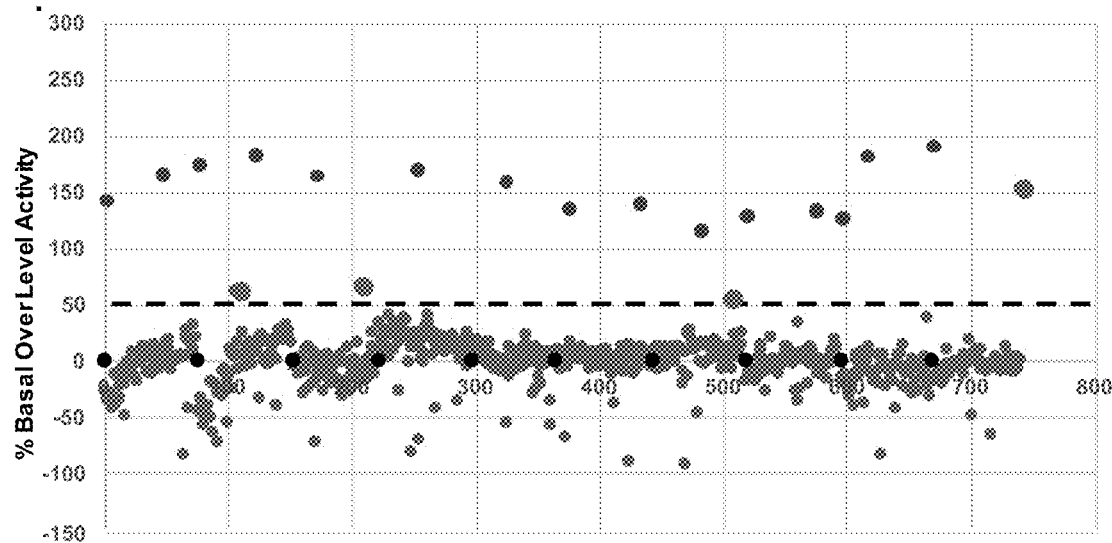
Figure 5:
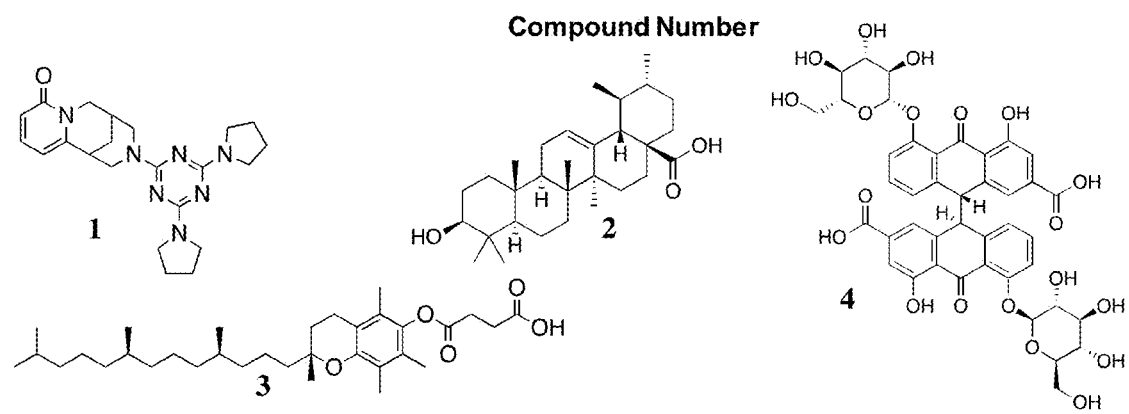

FIG. 5. (FIG. 5A) Scatter plot of screening results utilizing the CT-L FRET reporter. The black dots represent the triplicates of the 20S CP basal level, which was then normalized to zero for each plate of compounds. AM-404, a known 20S CP stimulator is the red dots which were included as positive controls in the screening plates. The green dots are the four hit molecules while the blue dots were not considered further. (FIG. 5B) Four primary hit molecules that stimulated the 20S CP at least 50%.

FIG. 6. Dose response curves for 20S CP stimulation for the three primary hits. The EC50's listed here is the concentration of half of the maximum stimulation. Molecule 3 stimulates the 20S CP the most with 150% (FIG. 6C) over basal level followed by molecule 2 at 100% (FIG. 6B) and molecule 3 at 50% (FIG. 6A).

FIG. 7. (FIG. 7A) Molecules 1-3 were tested for their ability to stimulate the 26S proteasome's CT-L activity. Only molecule 1 showed any stimulation ability. (FIG. 7B) The same molecules were tested with the iCP. The iCP has different active site subunits than the 20S CP but the game gate subunits. In this case, molecules 2 and 3 showed an effect, while 1 did not.

Figure 8:
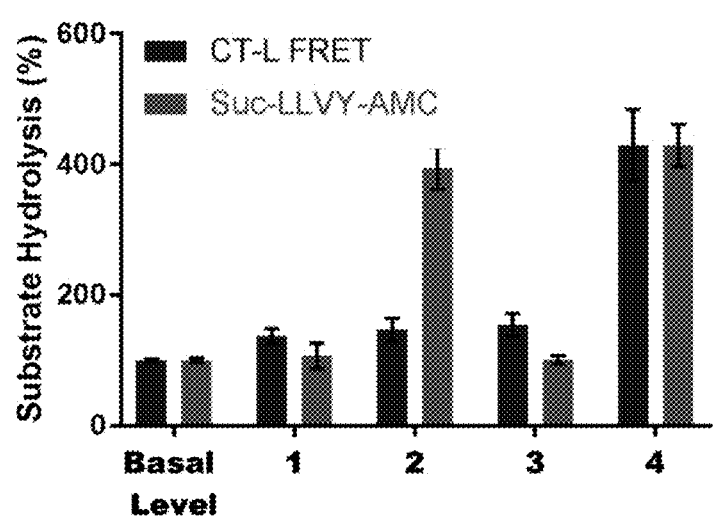

FIG. 8. Comparison of the activity of the four primary hits with the CT-L FRET and the 4-amino acid reporter for detecting 20S CP stimulation. Molecules 2 and 3 would not have been considered primary hits if we had utilized the smaller reporter.

Figure 9:
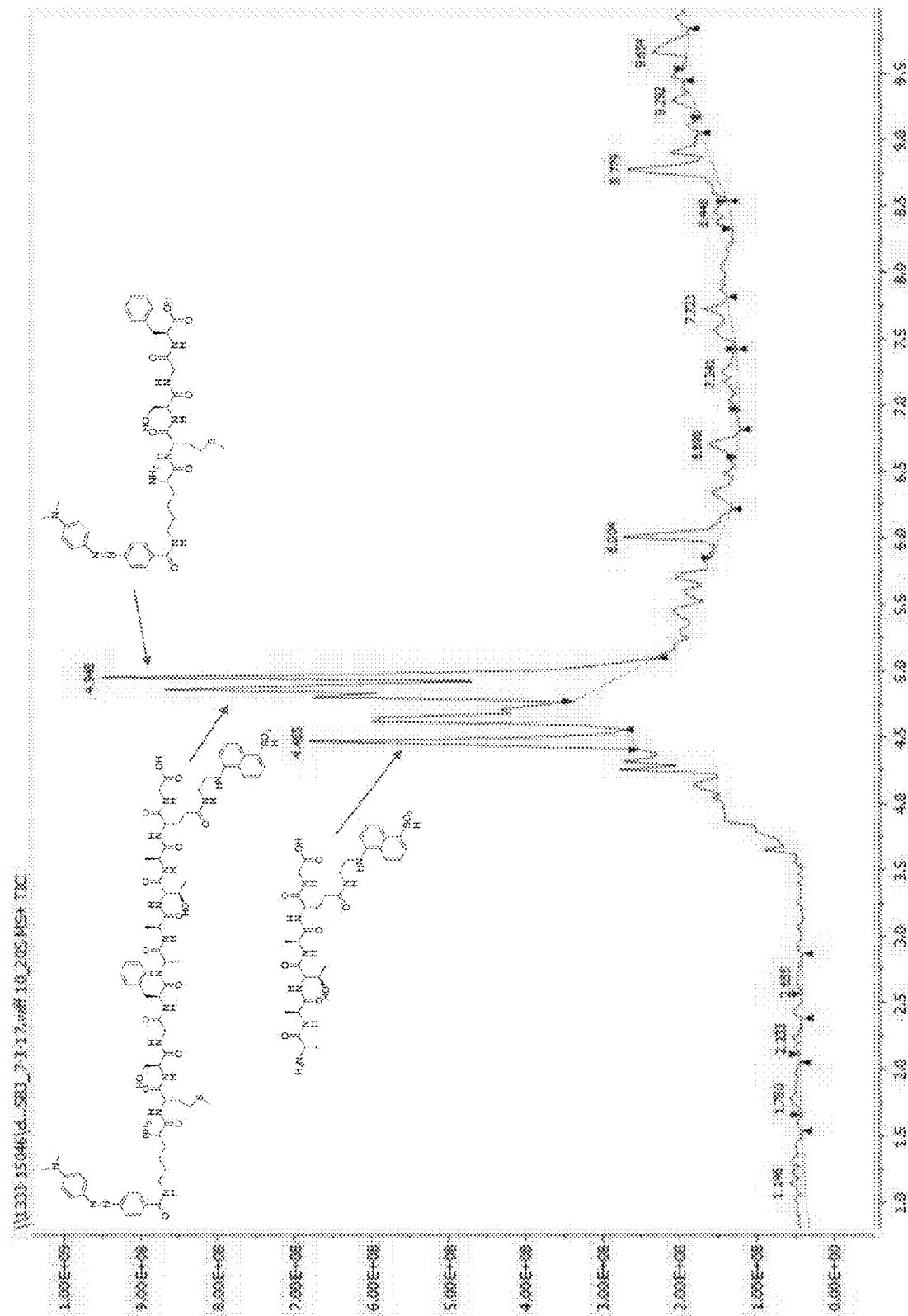

FIG. 9. LC-MS analysis of the CT-L FRET reporter hydrolysis by the 20S CP.

Figure 10:
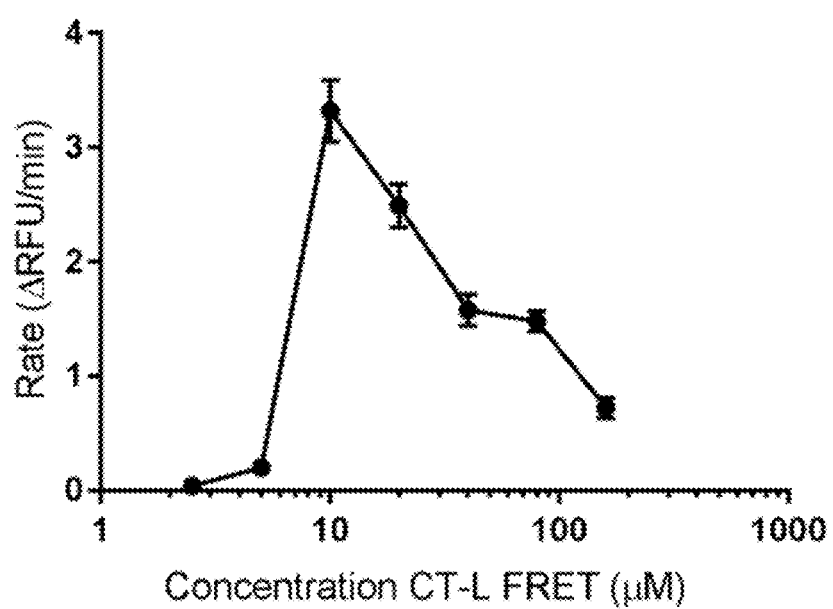

FIG. 10. Rate of hydrolysis of the CT-L FRET reporter of the 20S CP at the following concentrations of reporter: 2.5, 5, 10, 20, 40, 80, and 160 µM.

FIGS. 11A and 11B.

FIG. 11A. Rate of hydrolysis of Suc-LLVY-AMC (SEQ ID NO: 4) at the following concentrations of SDS: 0, 125, 250, 500, 1000, 2000, and 4000 µM.

FIG. 11B. Kinetic analysis of the addition of 500 µM or 1000 µM SDS compared to the basal activity of the 20S proteasome.

FIG. 12A, 12B, 12C.

FIG. 12A. Increase in the rate of hydrolysis of Bz-VGR-AMC in the presence of 500 µM SDS compared to the basal activity of the 20S CP: 2-fold.

FIG. 12B. Increase in the rate of hydrolysis of T-L FRET reporter in the presence of 500 µM SDS compared to the basal activity of the 20S CP: 5-fold.

FIG. 12C. A succinct comparison of the rate of hydrolysis of the T-L FRET reporter and Bz-VGR-AMC in the presence of 500 µM SDS. The control is the rate of hydrolysis by the 20S in the absence of a stimulator.

FIGS. 13A and 13B.

FIG. 13A Chemical structure of fenofibrate.

FIG. 13B Increase in fluorescence intensity in the presence of fenofibrate compared to control.

Figure 14:
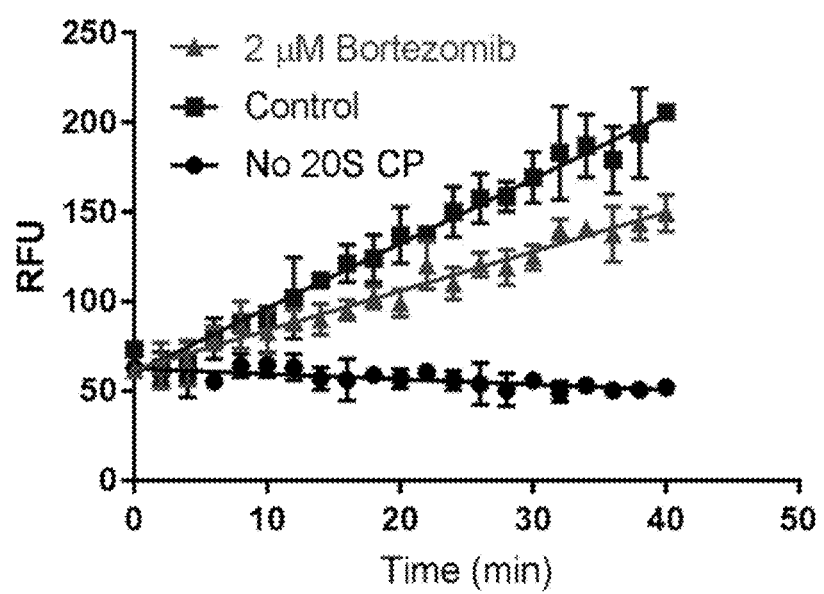

FIG. 14. Decrease in the rate of hydrolysis of the CT-L FRET reporter in the presence of 2 µM bortezomib: 40% decrease.

FIGS. 15A and 15B.

FIG. 15A. Kinetic analysis of the trypsin-like activity of the 20S CP in the presence of 25 µM of compounds 1, 2, and 3.

FIG. 15B. A succinct comparison of the rate of hydrolysis of the T-L FRET reporter by the 20S CP in the presence of 25 µM of compounds 1, 2, and 3. The basal level is the rate of hydrolysis by the 20S CP in the absence of a stimulator and is set to 100%.

Figure 16:
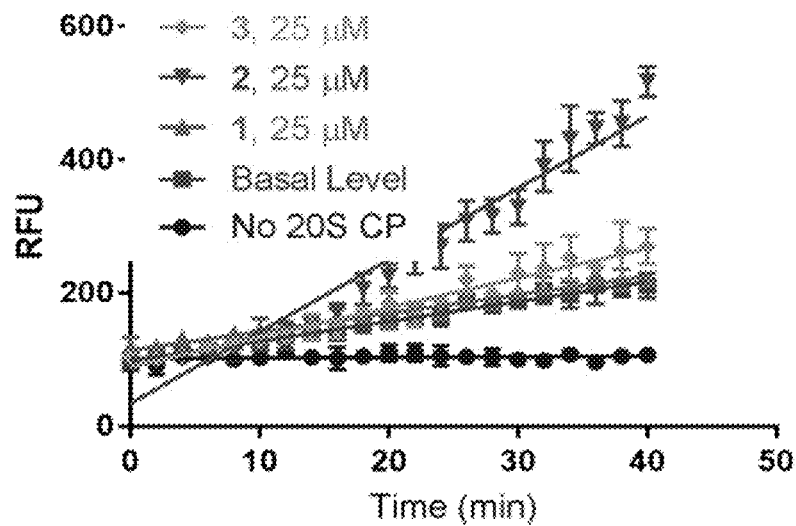
Figure 16:
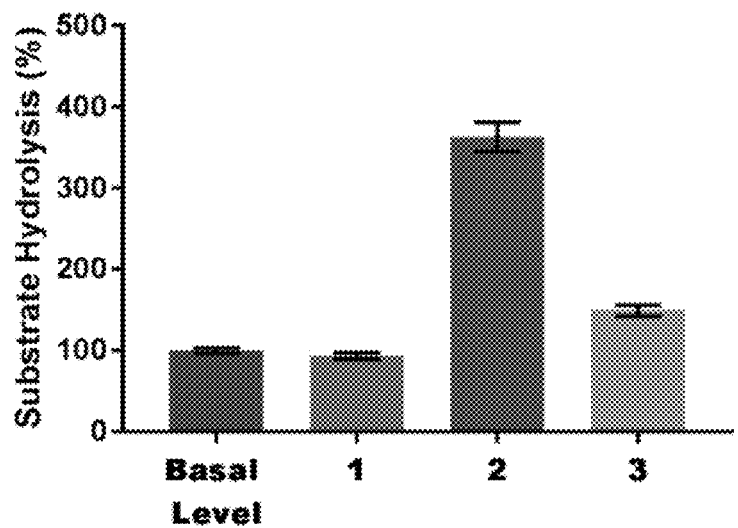

FIGS. 16A and 16B.

FIG. 16A. Kinetic analysis of the caspase-like activity of the 20S CP in the presence of 25 µM of compounds 1, 2, and 3.

FIG. 16B. A succinct comparison of the rate of hydrolysis of the CP-L FRET reporter by the 20S CP in the presence of 25 µM of compounds 1, 2, and 3. The basal level is the rate of hydrolysis by the 20S CP in the absence of a stimulator and is set to 100%.

FIGS. 17A and 17B.

FIG. 17A. Kinetic analysis of the chymotrypsin-like activity of the 26S proteasome in the presence of 25 µM of compounds 1, 2, and 3.

FIG. 17B. Kinetic analysis of the chymotrypsin-like activity of the immunoproteasome core particle (iCP) in the presence of 25 µM of compounds 1, 2, and 3.

FIG. 18. MALDI analysis of the CT-L FRET and T-L FRET reporters.

TABLE S1

Rate and standard deviation values for the basal activity of the 20S CP, stimulated activity in the presence of AM-404 (positive control), and activity in the presence of fenofibrate (negative control).

| Sample: | Mean Signal (Rate) | Standard Deviation |
|---|---|---|
| Basal (background) | 5.300 | 0.1376 |
| Positive Control | 40.46 | 1.210 |
| Negative Control | 5.795 | 0.1521 |

TABLE S2

Values obtained by inputting the data in Table S1 into the equations above.

| Standard | Value |
|---|---|
| S/N (pos) | 255.5 |
| S/B (pos) | 7.634 |
| % CV (pos) | 2.991 |
| % CV (neg) | 2.625 |
| Z' | 0.8821 |

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

To discover more biologically relevant 20S CP stimulating molecules and limit the false negative rate during a high throughput screening campaign, we have developed fluorescence resonance energy transfer reporters to monitor all three types of activity of the 20S CP, FIG. 2B. As we report here, these FRET reporters are over three-times more sensitive to stimulation than the traditionally utilized reporters. We utilized the chymotrypsin-like FRET reporter (CT-L FRET) to screen a library of 800 small molecules and discovered three that stimulate the 20S CP. Two molecules (compound were validated as 20S CP stimulating probes that elicit their effects through opening the gate, as both molecules increase the three types of 20S CP hydrolysis activity. The third molecule we present here, whose scaffold has been previously unreported to interact with the 20S CP, only stimulates the chymotrypsin-like activity of the 20S CP. This is the first time a molecule with this mechanism of action has been reported. This result highlights that our FRET reporters can discover both gate opening and allosteric stimulating probes.

The FRET reporters we present here have a number of advantages over the three to four amino acid-coumarin reporters used previously. First, as we demonstrated with the CT-L FRET reporter, it is 3.5-times more sensitive to stimulation of the 20S CP than Suc-LLVY-AMC (SEQ ID NO: 4), FIG. 3C. This is a major advantage when performing a high throughput screen of thousands of molecules. Not only are false negatives of great concern during screening, but so are false positives. Commonly, when performing a screen, primary hits will not be especially potent; therefore, it is essential to have a reporter sensitive enough to detect potential weak hits, limiting false negatives. When we screened 715 compounds with the CT-L FRET reporter, we detected four primary hits, giving a hit rate of 0.6%.

As a proof of concept on the sensitivity of the CT-L FRET reporter, we also tested these four primary hits with the Suc-LLVY-AMC (SEQ ID NO: 4) reporter to see if they would have been discovered. As shown in FIG. 8, molecules 1 and 3 would not have been considered primary hits if this library of molecules was screened with the Suc-LLVY-AMC (SEQ ID NO: 4) reporter. Not only will screening with the CT-L FRET reporter be able to detect more molecules when screening libraries previously untested for 20S CP stimulating molecules, it can also be used to re-screen libraries that were anticipated to have hits but did not.

Our method presented here for screening for new 20S CP stimulating molecules has a distinct advantage over screening in cells. While in cellulo screening does inherently report molecules that are able to enter the cell, the true biological target of the molecule can be very unclear. This is especially true when screening for proteasome stimulators. The term proteasome stimulator has a very broad definition. For example, there are a number of molecules that have been reported as proteasome stimulators or enhancers but actually make no interaction with the proteasome itself.[23,32] These molecules do affect the ability of the proteasome to degrade proteins but do so through interactions with deubiquitinases or proteasome-associated proteins. Additionally, current proteasome activity reporters cannot differentiate between the 20S CP and the 26S, and in the cell, both isoforms are present. While stimulating the 26S, either through ubiquitin-dependent or independent mechanisms, may be of interest, there is some cause for concern. First, it was recently reported that stimulating ubiquitin-dependent proteasome activity can actually help cancer cells to survive.[33] Second, as previously described, in diseased cells only the 20S CP is present, as the precursor proteins to form the 19S RP are not produced at high enough levels. Therefore, in these diseases, only the 20S CP is available to degrade accumulated proteins, and molecules that directly affect this isoform have the greatest potential to be tested as therapeutics. While 26S stimulating molecules may be of interest, screening for molecules should be focused on finding 20S CP stimulators, which cannot be done in a cell-based assay.

Concern has also been expressed on the toxic potential of molecules that stimulate this protease. Obviously, stimulating the 20S CP could have negative effects on cells by destroying proteins that are still required by the cell. However, we do not believe this will be the case. The 20S CP can only degrade small, intrinsically disordered proteins that are not ubiquitinated. The amount of proteins that fall into this category is relatively small, but does include toxic proteins such as tau and α-synuclein.[34] Even upon stimulation, the 20S CP cannot degrade proteins such as GFP, GAPDH, or actin in a ubiquitin-independent manner.[35] While there may be some toxicity associated with 20S CP stimulation, similar to what is observed with other drug mechanisms, based on the variety of molecules we have discovered here, we should be able to tailor the activity to the amount desired based on the disease or target of interest.

Although we only screened a very small library, we discovered three compounds that validated as 20S CP stimulators. Compound 3, which is vitamin E succinate, is an interesting result because of its long carbon tail. There have been a number of other molecules with similar features, including SDS and AM-404, that are believed to be gate openers of the 20S CP through a denaturing effect of the N-termini of the α-ring that makes up the gate. Compound 2, ursolic acid, is very similar in structure to betulinic acid, a previously reported 20S CP stimulator.[20] Both of these compounds, because of their substantial activity in other biochemical assays, are not ideal to begin in-depth cellular analysis on the effects of stimulating the 20S CP or animal experiments, but their scaffolds represent a starting point for medicinal chemistry studies. Clearly, molecules with an aliphatic carbon chain, whose length and unsaturation has yet to be determined, can act as 20S CP gate openers. Without being bound by any theory, a similar hypothesis can be made for the molecules with a steroid scaffold with stereochemistry and substitution similar to ursolic and betulinic acid. The triazine scaffold of molecule 1 is also an exciting medicinal chemistry avenue to explore.[36] Based on a PubChem search, this molecule has not been reported to be active in a significant amount of assays and is an easy scaffold to make a variety of derivatives to find more potent molecules. Synthesis and testing of derivatives of all three of these molecules may lead to other potent stimulators.

To begin our design of a more biologically relevant assay to discover 20S CP stimulating molecules, we attempted to have a larger reporter to yield hit molecules that had more of a potential to stimulate the 20S CP to accept an intrinsically disordered protein. We also wanted to have a reporter that was more challenging for the 20S CP to degrade without a stimulator present. The small reporter most often used, FIG. 2A, to monitor the chymotrypsin-like activity of the 20S CP can easily be turned over with no stimulating molecule present; because of this, it has a very limited dynamic range, meaning that the difference between the basal level of activity and stimulated activity of the 20S CP is very small. There have been other proteasome activity reporters developed, but these too are small peptides of three to four amino acids in length and are not appropriate for stimulation studies.[22] Reporters for monitoring the activity of the proteasome in cells have also been developed but cannot differentiate between activity of the 20S CP and the 26S proteasome.[23-25] There have also been gel- and NMR-based assays for detecting the activity of the 20S CP, but these are not amenable for high throughput screening.[26,27]

In addition to designing a larger reporter, we also wanted to move the hydrolysis site away from the C-terminus to a more central position. This requires that more of the reporter needs to be shuttled into the 20S CP, which would more accurately portray how a disordered protein would also fit in to be degraded. We wished to retain the speed and cost effectiveness of a fluorescent assay, which is why we ultimately decided on developing FRET probes. There were report of FRET peptide designed to monitor the activity of HIV protease, which uses the Dabcyl moiety as the FRET acceptor and Edans as the donor.[28] We synthesized the largest peptide we could to best mimic a disordered protein but still retain sufficient FRET efficiency to limit any background signal. The amino acids between the FRET pairs were also carefully chosen so that only one active site type was engaged during a screen. Our first FRET reporter was synthesized and tested to study the chymotrypsin-like activity of the 20S CP. At the fifth amino acid position is a phenylalanine, which is recognized by the beta-5 subunit of the 20S CP. Hydrolysis of this FRET reporter occurs at the C-terminal side of the phenylalanine (Supporting Information Figure S1). This cleavage event then allows the signal for Edans fluorescence to be obtained because it is no longer quenched by the Dabcyl moiety. Exchange of the phenylanine for an arginine or an aspartic acid allows one to monitor the trypsin- or caspase-like activity, respectively. The remaining amino acids were chosen based on cost effectiveness, ease of coupling, and to aid in buffer solubility. FIG. 2B shows the final reporter designs.

For all of our assays, we decided to monitor the 20S CP activity over 40 minutes, taking a reading every two minutes to generate a rate of hydrolysis ($\Delta$RFU/min). While every attempt was made to keep the basal level of the 20S CP constant, some loss of activity can occur for a variety of reasons from different batches. Monitoring the 20S CP activity over a range of time to generate a rate, rather than a single time point, minimizes the error from screen to screen. We next needed to determine the amount of FRET reporter and 20S CP in each well to obtain significant signal. Previous reports have utilized 250 µM of the Suc-LLVY-AMC (SEQ ID NO: 4) and between 1-10 nM of 20S CP to monitor the 20S CP activity. The first test with the CT-L FRET we repeated the 250 µM of reporter with 9 nM of 20S CP. Not surprisingly, this was too much reporter and led to confusing results. The CT-L FRET reporter was then tested at decreasing concentrations keeping the concentration of 20S CP at 9 nM. Excitingly, the CT-L FRET reporter had the best response at more than tenfold less (20 µM) than the Suc-LLVY-AMC (SEQ ID NO: 4) probe, FIG. 10.

To determine the increased sensitivity to stimulation the CT-L FRET reporter provides over the smaller reporter, we tested both in the presence of sodium dodecyl sulfate (SDS). SDS has long been considered a 20S CP stimulator.[29] It is believed that it denatures the gate opening to allow more substrate to enter, leading to an increase in the amount of fluorescence observed. After determining the $EC_{50}$ of SDS (FIG. 11), we compared the basal level of activity of the 20S CP to that in the presence of 500 µM of SDS with the CT-L FRET or the Suc-LLVY-AMC (SEQ ID NO: 4) reporter. For this analysis, the basal level of the 20S CP was set to 100% for both probes, and the percentage of increase in the rate of fluorescent accumulation per minute in the presence of SDS was determined. FIG. 3A shows the data obtained with the Suc-LLVY-AMC (SEQ ID NO: 4) reporter. The average basal level of the 20S CP with this reporter was determined to be 60 $\Delta$RFU/min, while in the presence of SDS, the rate increased to an average rate of 145 $\Delta$RFU/min, a 2.4-fold increase. The result with the CT-L FRET is shown in FIG. 3B. With this reporter, the average basal level of the 20S CP was determined to be 2.9 $\Delta$RFU/min, and after treatment with SDS, the rate increased to an average rate of 24 $\Delta$RFU/min, an 8.3-fold increase in the rate.

The CT-L FRET is hydrolyzed at a much slower rate compared to the Suc-LLVY-AMC (SEQ ID NO: 4) reporter. While this is significant, what is most noteworthy is the dramatic increase in the difference between basal level and stimulated activities of the 20S CP, FIG. 3C. The stimulation that SDS can induce is considered the maximum increase in activity the 20S CP can exhibit by the gate opening mechanism. Therefore, the range of molecules our CT-L FRET reporter can detect during a high throughput screening campaign is larger than that of the Suc-LLVY-AMC (SEQ ID NO: 4) probe, as it is 3.5-fold more sensitive to stimulation. A similar result was observed when comparing the smaller trypsin-like reporter to our larger FRET reporter, FIG. 11.

To confirm that the CT-L FRET reporter could detect stimulators in a dose response manner and that the result with SDS was not due to an interaction between the CT-L FRET reporter and SDS, we also tested a previously reported 20S CP stimulator.[30] AM-404, FIG. 4A, has been identified as a 20S CP stimulator with the Suc-LLVY-AMC (SEQ ID NO: 4) with an $EC_{50} \approx 32$ µM in cellulo. In a similar fashion as the SDS experiment, purified 20S CP was dosed with decreasing amounts of AM-404. As shown in FIG. 4B, AM-404 stimulates the 20S CP with the CT-L FRET reporter. At the lowest concentration we tested, AM-404 stimulated the activity of the 20S CP 4-fold. As a negative control, we tested fenofibrate, another hydrophobic molecule, with the CT-L FRET probe and the 20S CP. At a variety of doses, this molecule did not stimulate the 20S CP, FIG. 12. With all of these results in mind, we can conclude that the CT-L FRET reporter can effectively detect 20S CP stimulating molecules and do so in a dose-dependent manner.

We next wanted to utilize the CT-L FRET reporter to screen a library of small molecules to find new 20S CP stimulating molecules. We screened the TimTec NPL-800 library, which is 800 natural products or natural product derivatives. The library was first pre-screened at 25 µM with no 20S CP over 40 minutes, looking for any change in fluorescence at the emission wavelength of Edans. Any molecule that showed a change in signal was excluded from screening. Additionally, this prescreen was used to determine what background, if any, to remove from the screening results with the 20S CP. Next, fresh 96-well plates were prepared that contained 25 µM of the compound, 20 µM of the CT-L FRET reporter, and 9 nM of 20S CP in a total volume of 50 µL. The plate was transferred to a fluorescent plate reader at 37° C. and a reading was taken every two minutes over a 40 minute period. This was performed until all 715 compounds were screened. 85 compounds were not screened with 20S CP because they did not pass our pre-screening qualifications. Wells containing 25 µM of AM-404, wells with no 20S CP, and wells to monitor the basal level of the 20S CP were included in triplicate in every plate. After all compounds were screened in singlet, the rates of 20S CP hydrolysis in the presence of each compound was calculated and compared to the basal level, FIG. 5A and FIG. 13. We decided to select hits as those that increased the rate of hydrolysis at least 50%. For cell experiments, we did not want to dose with more than 25 µM, but a 50% increase in the biochemical assay should provide enough stimulation in cells to see a desired signal. After this analysis, four compounds were considered primary hits, FIG. 5B.

To validate these four compounds as 20S CP stimulating probes, we performed a number of additional assays with newly purchased compound. First, the four hits were tested in triplicate at 25 µM, just as was performed in the primary screen. Molecules 4, Sennoside B, did not perform as it had in the initial screen. After liquid chromatography-mass spectrometry analysis of the compound from the screening library and the new solid obtained, a significant amount of the non-glycosylated product was seen in the new stock. At this point, compound 4 was removed from the hit pool due to the difficulty in obtaining pure product to test and its overall poor drug-like properties. However, molecules 1-3 validated in triplicate at 25 µM. Since we had only ever tested the molecules at 25 µM, we chose to perform a dose response curve for all three. As shown in FIG. 6A-C, all three compounds responded in a dose response manner. Molecule 3 is the most potent with an $EC_{50}$ of 7 µM, followed by compound 1 with an $EC_{50}$ of 10 μM, and compound 2 with an $EC_{50}$ of 14 μM.

As previously mentioned the 20S CP has three types of active sites: chymotrypsin-, trypsin- and caspase-like. Until now, we have only monitored the increased activity of the chymotrypsin-like site of the 20S CP. We wished to assess whether these three molecules are behaving as 20S CP gate openers or interacting more specifically with a designated active site. If a molecule is increasing the hydrolysis rate of the 20S CP by opening the gate to allow more substrates to enter, the turnover rate of all three active sites should increase. If a compound behaves as an allosteric stimulator, only one active site should see an increase in hydrolysis. To determine if our newly discovered molecules elicit their stimulation effects either as a gate opener or allosteric stimulator, we synthesized two additional FRET reporters. The phenylalanine in the CT-L FRET reporter was exchanged with an arginine to monitor the trypsin-like activity (T-L FRET) or with an aspartic acid to evaluate the caspase-like activity (CP-L FRET) of the 20S CP. Molecules 1-3 were first tested with the T-L FRET reporter. At 25 μM, 2 and 3 stimulated the trypsin-like activity of the 20S CP, 234% and 146%, respectively, FIG. 15. A similar result was obtained with the CP-L FRET reporter, FIG. 16. Most interestingly, 1 did not affect the trypsin- or caspase-like activities of the 20S CP. From these results, we can infer that 2 and 3 act as 20S CP gate openers, while 1 only increases the chymotrypsin-like activity of the 20S CP, potentially through an allosteric interaction with the beta-5 subunit. To the best of our knowledge, this is the first example of a small molecule that directly interacts with the 20S CP to stimulate only the chymotrypsin-like activity.

As previously described, the 20S CP can be capped with the 19S RP to enable ubiquitin-dependent protein degradation. The 19S RP associates directly with the alpha-ring of the 20S CP, opening the gate to allow substrates to enter. Molecules that behave as gate openers should therefore have no effect on the 26S proteasome because the gate is already open through the interaction with the 19S RP. This is indeed the case with compounds 2 and 3, FIG. 7A. Neither molecules 2 or 3 affected the rate of the 26S proteasome, providing more evidence these molecules behave by opening the gate of the 20S CP. Molecule 1 does increase 26S stimulation by 44%. This result further supports our mechanistic hypothesis that 1 interacts with the beta-5 subunit as it stimulates both the 20S and 26S isoforms of the proteasome.

To further evaluate the mechanism of action of compounds 1-3, they were tested for their ability to stimulate the activity of the immunoproteasome (iCP). The iCP and 20S CP contain the same protein subunits that form the gate, but the active site subunits are slightly different. Interferon-gamma stimulates the production of the iCP active sites, which cleave proteins into peptides differently than the 20S CP does. The peptides produced by the iCP are typically more amenable to be loaded into an MHC-I complex. To support our hypothesis that compounds 2 and 3 are gate openers, they were tested for their ability to stimulate the iCP since the gate subunits are identical to the 20S CP. As shown in FIG. 7B compounds 2 and 3 do stimulate the chymotrypsin-like activity of the iCP significantly, while compound 1 shows essentially no increase in activity. This result implies that molecule 1 has a specific interaction with the beta-5 subunit of the 20S CP and less so with the beta-5i subunit of the iCP. The sequences of the beta-5 and the beta-5i subunits are very similar with the exception of the residues surrounding the active site threonine residue, called the S1 binding pocket.[31] This potentially is where molecule 1 binds.

General Materials and Methods

Utilizing solid-phase peptide synthesis, the probes were synthesized using Fmoc-Gly-Wang resin, and the reactions were performed in fritted syringes (purchased from Henke Sass Wolfe). Resin was purchased from Chem-Impex Int'l INC. F-moc protected natural amino acids were purchased from Novabiochem. Fmoc-Glu(EDANS)-OH and Fmoc-Lys (Dabcyl)-OH were purchased from Chem-Impex Int'l INC. COMU was purchased from Alfa Aesar. N,N-Diisopropyl-ethylamine was purchased from Fisher Scientific. Piperidine was purchased from Sigma Aldrich. Dichloromethane and N,N-Dimethylformamide were purchased from Fisher Scientific.

Probe purification was performed on an Agilent HPLC, using a reversed phase column. Samples were detected using a UV lamp, looking specifically at 254 nm and 280 nm wavelengths. All sample analysis was initiated with an isocratic elution of 95% A at 14 mL/min for # min followed by a linear gradient of 5%-95% B at 14 mL/min over ## min, then an isocratic elution for # min at ##% B, and re-equilibration with ##% A for # min (A: $H_2O$, 0.1% formic acid; B: $CH_3CN$, 0.1% formic acid). Once samples were purified, fractions were collected, combined, and lyophilized, using SPECIFIC Lyophilizer.

Probe analysis was performed using MALDI imaging mass spectrometry.

Each probe was dissolved in dimethylsulfoxide (DMSO: for molecular biology, purchased from Sigma Aldrich) and diluted using Tris-HCl (50 mM, pH 7.7, purchased from Fisher Scientific). AM-404 was purchased from Tocris. Sodium dodecyl-sulfate was purchased from Alfa Aesar. Bortezomib was purchased from INSERT NAME. Natural Products Library was purchased from TimTec, LLC. Purified 20S Proteasome was purchased from Enzo Life Sciences, INC. Assays were performed with a 96-well plate (black, Cat. 237108, ThermoFisher Scientific) using the Synergy 4 Plate Reader.

Probe Synthesis

To a 3 mL fritted syringe was added 49.9 mg (0.065 meq, 1 eq) Fmoc-Gly-Wang resin (0.658 meq/g). The resin was swelled in 2 mL 1:1 DCM:DMF for 1 hr. The DCM:DMF was drained using apparatus. Each coupling of the amino acids was performed using 4 eq amino acid, 4 eq COMU, and 8 eq DIPEA. The amino acid and COMU were dissolved in 1 mL DMF. DIPEA was added, and the solution was vortexed for 2 min before being added to the resin. Each coupling of the Fmoc-protected amino acids was performed for 1 hr at 60° C. while shaking at 400 rpm. Following each coupling, the resin was rinsed six times: three times with 1 mL DMF followed by three washes with 1 mL DCM. After the final wash, the Kaiser test was performed to determine the completion of the coupling reaction. Once the coupling was determined successful, the Fmoc was removed by adding 2 mL 20% piperidine in DMF to the resin in the reaction vessel, which was shaken at room temperature for 40 min. Following deprotection, the resin was rinsed six times: three times with 1 mL DMF followed by three washes with 1 mL DCM. After the final rinse, the Kaiser test was performed to determine the completion of the deprotection. If the Kaiser test showed the coupling or deprotection as unsuccessful, the reaction was repeated under the same conditions. The peptide was cleaved by adding a solution of 1.9 mL trifluoroacetic acid, 500 μL DCM, and 500 μL triisopropylsilane to the resin. The reaction vessel was shaken at room temperature for 2 hr. The solution was then allowed to drip into a 15 mL falcon tube. The resin was rinsed three times with 1 mL DCM, and the rinses were also allowed to drip into the 15 mL falcon tube. The solution was evaporated under a gentle stream of argon, leaving a red-colored residue.

To the residue was added 5 mL ether. The tube was vortexed for 1 min as the peptide crashed out of solution. The solution was then centrifuged for 1 min at 4700 rpm, and the ether was decanted. This was repeated two more times. After the ether was decanted for the final time, a 16-gauge needle was used to make a small hole near the cap of the 15 mL falcon tube, which was placed in a vacuum-sealed container to remove the remaining ether.

Probe Purification

The peptide was dissolved in 3 mL DMSO and 1 mL 1:1 DMSO:$H_2O$. Purification was performed using an Agilent HPLC.

All sample analysis was initiated with an isocratic elution of 95% A at 14 mL/min for 3 min followed by a linear gradient of 5%-95% B at 14 mL/min over 12 min, then an isocratic elution for 3 min at 95% B, and re-equilibration with ##% A for # min (A: $H_2O$, 0.1% trifluoroacetic acid; B: $CH_3CN$, 0.1% trifluoroacetic acid). Once samples were purified, fractions were collected, combined, and lyophilized, using SPECIFIC Lyophilizer. The mass of the lyophilized FRET reporter was determined to be 5.1 mg, producing a 5% yield CT-L FRET Reporter Hydrolysis by the 20S CP The lyophilized CT-L FRET reporter was dissolved in dimethylsulfoxide (for molecular biology) and diluted with Tris-HCl (50 mM, pH 7.7) to create a 10 μM CT-L FRET solution.

To verify that the CT-L FRET reporter was being hydrolyzed by the chymotrypsin-like activity of the 20S core particle (20S CP), this reporter was incubated in triplicate with and without the 20S CP for 2 hr at 37° C. The samples were prepared in a black 96-well plate thus: to each well was added 40 μL 10 μM CT-L FRET (in Tris-HCl, 50 mM, pH 7.7). To the control wells was added 10 μL Tris-HCl. To the test wells was added 5 μL Tris-HCl and 5 μL 90 nM 20S CP in Tris-HCl (final concentration of 9 nM). The 96-well plate was incubated for 2 hr at 37° C. Following incubation, the control samples were combined in a 0.600 mL epitube. This was repeated for the test wells. ThermoScientific 100 μL C18 tips were then used to transfer the peptides in the control and samples tubes from Tris-HCl into a 1:1 solution of $H_2O$:Acetonitrile with 0.1% formic acid (FA). This was done following the procedure provided by the manufacturer. Briefly, the samples were adjusted to 0.2% trifluoroacetic acid (TFA) by adding 15 μL 2.5% TFA to each sample. The C18 tip was wet by aspirating then discarding 100 μL of 1:1 $H_2O$:Acetonitrile. This was repeated once. The C18 tip was then equilibrated by aspirating then discarding 100 μL 0.1% TFA in water. This was repeated once. To obtain the peptides, 100 μL of the control sample was aspirate and dispensed 10 times. After the final aspiration, the sample volume was discarded. The C18 tip was rinsed by aspirating and discarding 100 μL 0.1% TFA 95:5 $H_2O$:Acetonitrile. This was repeated once. The sample was eluted using 50 μL 0.1% FA in 1:1 $H_2O$:Acetonitrile. This procedure was followed for both the control sample and the test sample. The elutions of these samples were then analyzed using the LC-MS. (FIG. 9).

Kinetic Screening Assay

Plate preparation for the kinetic assay was performed similarly for all assays. All 96-well plates contained the following in triplicate: reporter background, containing reporter only, and control wells, containing reporter and purified 20S CP. It was determined that each well will contain a total volume of 50 μL. To each well was added 40 μL of the coumarin or FRET reporters (in Tris-HCl, 50 mM, pH 7.7). To the reporter background wells was added 7.5 μL Tris-HCl and 2.5 μL of the solvent in which the compound of interest was dissolved or diluted. Similarly, to the control wells was added 2.5 μL Tris-HCl and 2.5 μL of the solvent in which the compound of interest was dissolved or diluted. To the test wells was added 2.5 μL Tris-HCl and 2.5 μL of the compound of interest at a predetermined concentration. Immediately prior to running the assay on the Synergy 4 Plate Reader, 5 μL purified 20S proteasome (90 nM in Tris-HCl) was added to the control and test wells.

The Synergy 4 Plate Reader was set to heat the plate at 37° C. and read fluorescence every 2 min over a 40 min period. The excitation and emission wavelengths were set according to the reporter. For the FRET reporter, the excitation and emission wavelengths were set to 335 nm and 493 nm, respectively, corresponding to the excitation and emission wavelengths of the Edans fluorophore. For the coumarin reporter, the excitation and emission wavelengths were set to 380 nm and 460 nm, respectively.

Determining Concentration of FRET reporter for Kinetic Assay

The lyophilized CT-L FRET reporter was dissolved in 400 μL dimethylsulfoxide (for molecular biology), producing an 8127.3 μM stock solution. This stock solution was used to make solutions of the FRET reporter at the following concentrations in Tris-HCl (50 mM, pH 7.7): 160, 80, 40, 20, 10, 5, and 2.5 μM. The following concentrations were verified using the Nano-drop, reading absorbance at 335 nm, the excitation wavelength of Edans: 160, 80, 40, and 20 μM. The lower concentrations of FRET reporter had corresponding absorbance values too low to be accurately measured by the Nano-drop.

These FRET reporter solutions were used in the kinetic assay in order to determine the appropriate concentration of reporter to be used in a high-throughput screening campaign. For each concentration, background and test wells were prepared in triplicate. The background wells were prepared thus: to each well was added 40 μL FRET reporter and 10 μL Tris-HCl (50 mM, pH 7.7). To each of the test wells was added 40 μL FRET reporter and 5 μL Tris-HCl. Immediately prior to performing the assay on the Synergy 4 Plate Reader, 5 μL purified 20S proteasome (90 nM in Tris-HCl) was added to the test wells, totaling the well volume at 50 μL (final concentration of 9 nM 20S proteasome). The Synergy 4 Plate Reader was set to heat the plate at 37° C. and read fluorescence every 10 min over a 2 hr period. The excitation and emission wavelengths were set to 335 nm and 493 nm, respectively. The resulting data in relative fluorescence units (RFU) was analyzed using GraphPad Prism and was plotted against time in minutes. The rate of hydrolysis (in ΔRFU/min) of the CT-L FRET reporter at each of the concentrations was plotted against its corresponding concentration, FIG. 10. Based on the resulting curve and the inability to validate the concentrations of 10 μM CT-L FRET using the Nano-drop, it was determined that 20 μM FRET reporter was the appropriate concentration to use for the screening kinetic assay.

Determining Concentration of SDS

Sodium dodecyl sulfate (SDS) was used to test the effect stimulating the 20S proteasome has on the hydrolysis of the FRET reporters. The appropriate concentration of SDS to use in the kinetic assay was determined using the small chymotrypsin-like activity reporter, Suc-LLVY-AMC (SEQ ID NO: 4). For accurate comparison, the Suc-LLVY-AMC (SEQ ID NO: 4) was prepared as a 20 µM solution in Tris-HCl (50 mM, pH 7.7). In triplicate, the following final concentrations of SDS were analyzed for the effect each has on the activity of the 20S proteasome: 4000 µM, 2000 µM, 1000 µM, 500 µM, 250 µM, 125 µM, and 0 µM, the basal activity of the 20S proteasome. To each well was added 40 µL 20 µM reporter (in Tris-HCl) and 2.5 µL Tris-HCl. Solutions of SDS were prepared in Tris-HCl at the following concentrations, corresponding to the final concentrations of SDS aforementioned: 80 mM, 40 mM, 20 mM, 10 mM, 5 mM, 2.5 mM, and 0 mM SDS, respectively. From these solutions, 2.5 µL was added to the appropriate wells in the 96-well plate. Immediately prior to reading the plate with the Synergy 4 plate reader, 5 µL purified 20S proteasome (90 nM in Tris-HCl) was added to the wells at a final concentration of 9 nM per well.

The Synergy 4 Plate Reader was set to heat the plate at 37° C. and read fluorescence every 2 min over a 1 hr period. The excitation and emission wavelengths were set to 380 nm and 460 nm, respectively, corresponding to the excitation and emission wavelengths of coumarin. The resulting data in relative fluorescence units (RFU) was analyzed using GraphPad Prism and was plotted against time in minutes. The rate of hydrolysis (in ΔRFU/min) of the Suc-LLVY-AMC (SEQ ID NO: 4) reporter at each of the concentrations of SDS was plotted against its corresponding concentration, FIG. 11a. Based on the resulting curve and the hyperbolic curve obtained using 1000 µM SDS (FIG. 11b), it was determined that 500 µM SDS was the appropriate concentration to use to test the effect stimulating the 20S proteasome has on the hydrolysis of the FRET reporters.

SDS Stimulation of the 20S CP

Stimulation of the 20S proteasome with SDS was determined using both the coumarin and FRET reporters for the chymotrypsin-like and trypsin-like activities of the 20S CP. To each well was added 40 µL of the coumarin or FRET reporters (in Tris-HCl, 50 mM, pH 7.7). To the reporter background wells was added 10 µL Tris-HCl (50 mM, pH 7.7) Similarly, to the control wells was added 5 µL Tris-HCl. To the test wells was added 2.5 µL Tris-HCl and 2.5 µL 10 mM SDS in Tris-HCl. Immediately prior to running the assay on the Synergy 4 Plate Reader, 5 µL purified 20S proteasome (90 nM in Tris-HCl) was added to the control and test wells. The assay was performed using the Synergy 4 plate reader as described for the general screening kinetic assay procedure.

AM-404 Stimulation of the 20S CP

AM-404 was used as a positive control compound to test the dose-response screening capabilities of the CT-L FRET reporter. The following concentrations of AM-404 were tested in triplicate: 50, 25, and 12.5 µM. To each well was added 40 µL 20 µM CT-L FRET (in Tris-HCl, 50 mM, pH 7.7). To the reporter background wells was added 5 µL Tris-HCl and 5 µL 1:1 Tris-HCl:DMSO. Similarly, to the control wells was added 5 µL 1:1 Tris-HCl:DMSO. To the 50 µM AM-404 test wells was added 2.5 µL Tris-HCl and 2.5 µL 1000 µM AM-404 in DMSO. To the 25 µM AM-404 test wells was added 2.5 µL Tris-HCl and 2.5 µL 500 µM AM-404 in DMSO. To the 12.5 µM AM-404 test wells was added 2.5 µL Tris-HCl and 2.5 µL 250 µM AM-404 in DMSO. Immediately prior to running the assay on the Synergy 4 Plate Reader, 5 µL purified 20S proteasome (90 nM in Tris-HCl) was added to the control and test wells. The assay was performed using the Synergy 4 plate reader as described for the general screening kinetic assay procedure.

Effect of Fenofibrate on the 20S CP

Fenofibrate was used as a negative control compound to test the dose-response screening capabilities of the CT-L FRET reporter. The following concentrations of fenofibrate were tested in triplicate: 50, 25, and 12.5 µM. To each well was added 40 µL 20 µM CT-L FRET (in Tris-HCl, 50 mM, pH 7.7). To the reporter background wells was added 5 µL Tris-HCl and 5 µL 1:1 Tris-HCl:DMSO. Similarly, to the control wells was added 5 µL 1:1 Tris-HCl:DMSO. To the 50 µM fenofibrate test wells was added 2.5 µL Tris-HCl and 2.5 µL 1000 µM fenofibrate in DMSO. To the 25 µM fenofibrate test wells was added 2.5 µL Tris-HCl and 2.5 µL 500 µM fenofibrate in DMSO. To the 12.5 µM fenofibrate test wells was added 2.5 µL Tris-HCl and 2.5 µL 250 µM fenofibrate in DMSO. Immediately prior to running the assay on the Synergy 4 Plate Reader, 5 µL purified 20S proteasome (90 nM in Tris-HCl) was added to the control and test wells. The assay was performed using the Synergy 4 plate reader as described for the general screening kinetic assay procedure.

Bortezomib Inhibition of the 20S CP

Bortezomib was used test the capabilities of the CT-L FRET reporter to detect inhibitors of the 20S CP. Bortezomib was tested at a concentration of 2 µM in triplicate. To each well was added 40 µL 20 µM CT-L FRET (in Tris-HCl, 50 mM, pH 7.7). To the reporter background wells was added 5 µL Tris-HCl and 5 µL 1:1 Tris-HCl:DMSO Similarly, to the control wells was added 5 µL 1:1 Tris-HCl:DMSO. To the test wells was added 2.5 µL Tris-HCl and 2.5 µL 40 µM bortezomib in DMSO. Immediately prior to running the assay on the Synergy 4 Plate Reader, 5 µL purified 20S proteasome (90 nM in Tris-HCl) was added to the control and test wells.

The assay was performed using the Synergy 4 plate reader as described for the general screening kinetic assay procedure.

Effect of 26S Stimulators on the 20S CP

Loperamide HCl and cyclosporin A have been shown to stimulate the 26S proteasome at concentrations as low as 5 µM. This concentration was used to test the effect of these compounds on hydrolysis of the CT-L FRET by the 20S CP.

Each compound was tested at a concentration of 5 µM in triplicate. To each well was added 40 µL 20 µM CT-L FRET (in Tris-HCl, 50 mM, pH 7.7). To the reporter background wells was added 5 µL Tris-HCl and 5 µL 1:1 Tris-HCl:DMSO Similarly, to the control wells was added 5 µL 1:1 Tris-HCl:DMSO. To the loperamide HCl test wells was added 2.5 µL Tris-HCl and 2.5 µL 100 µM loperamide HCl in DMSO. To the cyclosporin A test wells was added 2.5 µL Tris-HCl and 2.5 µL 100 µM cyclosporin A in DMSO. Immediately prior to running the assay on the Synergy 4 Plate Reader, 5 µL purified 20S proteasome (90 nM in Tris-HCl) was added to the control and test wells.

The assay was performed using the Synergy 4 plate reader as described for the general screening kinetic assay procedure.

Screening Natural Product Library

The natural product library of 800 compounds was purchased as ten 96-well plates of 80 compounds from TimTec LLC. Each compound had been dissolved in 50 µL of DMSO to produce a 10 mM solution of compound. A diluted stock of each plate was made by pipetting 4 µL of 10 mM compound into 76 µL DMSO in a corresponding 96-well plate. Then, 80 µL Tris-HCl (50 mM, pH 7.7) was added to produce a final concentration of 250 µM of compound in 1:1 DMSO:Tris-HCl.

Due to the 96-well vessel containing 80 compounds in stock solutions, 80 compounds were screened in each 96-well plate. Prior to performing the screen with the 20S CP, background plates were prepared and analyzed in 96-well plates for the compounds of interest. To these wells was added 45 µL Tris-HCl and 5 µL of the compound of interest at 250 µM in 1:1 Tris-HCl:DMSO, generating 25 µM a final concentration of compound in each well. The assay was then performed using the Synergy 4 plate reader as described for the general screening kinetic assay procedure. This was done in order to determine the amount of background fluorescence exhibited by each compound. Those compounds exhibiting a significant change in fluorescence signal over time were excluded from screening.

The remaining compounds were then screened in singlet with the 20S CP; however, each plate was screened with the following in triplicate: CT-L FRET background, CT-L FRET control (containing reporter and purified 20S CP), and a positive control (containing reporter, purified 20S CP, and 25 µM AM-404). To each well was added 40 µL 20 µM reporter (in Tris-HCl). To the reporter background wells was added 5 µL Tris-HCl and 5 µL 1:1 Tris-HCl:DMSO. Similarly, to the controls wells was added 5 µL 1:1 Tris-HCl:DMSO. To the test wells was added 5 µL of the compound of interest at 250 µM in 1:1 Tris-HCl:DMSO (final concentration of 25 µM). Immediately prior to running the assay on the Synergy 4 Plate Reader, 5 µL purified 20S proteasome (90 nM in Tris-HCl) was added to the control and test wells.

The assay was performed using the Synergy 4 plate reader as described for the general screening kinetic assay procedure.

Validating Hit Compounds in Triplicate

A 500 µM solution was made for each of the hit compounds (1, 2, 3, and 4) in DMSO by diluting the 10 mM stock solution purchased from TimTec, LLC. The stimulation capabilities of the compounds were then tested in triplicate using the CT-L FRET reporter.

To each well was added 40 µL 20 µM reporter (in Tris-HCl). To the reporter background wells was added 5 µL Tris-HCl and 5 µL 1:1 Tris-HCl:DMSO Similarly, to the controls wells was added 5 µL 1:1 Tris-HCl:DMSO. To the test wells was added 2.5 µL Tris-HCl and 2.5 µL of the 500 µM solution of the compound of interest in DMSO (final concentration of 25 µM). Immediately prior to running the assay on the Synergy 4 Plate Reader, 5 µL purified 20S proteasome (90 nM in Tris-HCl) was added to the control and test wells.

Background wells were prepared in singlet for the compounds of interest. To these wells was added 47.5 µL Tris-HCl and 2.5 µL of the 500 µM solution of the compound of interest in DMSO.

The assay was performed using the Synergy 4 plate reader as described for the general screening kinetic assay procedure.

Once validated, it was discovered that compounds 2, 3, and 4 could be purchased more cheaply from other sources. These compounds were bought from Sigma Aldrich and then tested in the manner previously stated.

Screening Hit Compounds with Suc-LLVY-AMC (SEQ ID NO: 4)

Similarly, a 500 µM solution was made for each of the hit compounds (1, 2, 3, and 4) in DMSO by diluting the 10 mM stock solution purchased from TimTec, LLC. The stimulation capabilities of the compounds were then tested in triplicate using the Suc-LLVY-AMC (SEQ ID NO: 4) reporter.

To each well was added 40 µL 20 µM reporter (in Tris-HCl). To the reporter background wells was added 5 µL Tris-HCl and 5 µL 1:1 Tris-HCl:DMSO Similarly, to the controls wells was added 5 µL 1:1 Tris-HCl:DMSO. To the test wells was added 2.5 µL Tris-HCl and 2.5 µL of the 500 µM solution of the compound of interest in DMSO (final concentration of 25 µM). Immediately prior to running the assay on the Synergy 4 Plate Reader, 5 µL purified 20S proteasome (90 nM in Tris-HCl) was added to the control and test wells.

Background wells were prepared in singlet for the compounds of interest. To these wells was added 47.5 µL Tris-HCl and 2.5 µL of the 500 µM solution of the compound of interest in DMSO.

The assay was performed using the Synergy 4 plate reader as described for the general screening kinetic assay procedure.

Screening 1, 2, and 3 with T-L FRET

The ability of compounds 1, 2, and 3 to stimulate the trypsin-like activity of the 20S CP was tested by screening these compounds in triplicate using the T-L FRET reporter.

To each well was added 40 µL 20 µM T-L FRET reporter (in Tris-HCl, 50 mM, pH 7.7). To the reporter background wells was added 5 µL Tris-HCl and 5 µL 1:1 Tris-HCl:DMSO. Similarly, to the control wells was added 5 µL 1:1 Tris-HCl:DMSO. To the test wells was added 2.5 µL Tris-HCl and 2.5 µL of a 500 µM solution of the compound of interest in DMSO. This resulted in a final concentration of 25 µM of the compound in the 96-well plate. Immediately prior to running the assay on the Synergy 4 Plate Reader, 5 µL purified 20S proteasome (90 nM in Tris-HCl) was added to the control and test wells.

The assay was performed using the Synergy 4 plate reader as described for the general screening kinetic assay procedure.

Screening 1, 2, and 3 with T-L FRET

The ability of compounds 1, 2, and 3 to stimulate the caspase-like activity of the 20S CP was tested by screening these compounds in triplicate using the CP-L FRET reporter.

To each well was added 40 µL 20 µM CP-L FRET reporter (in Tris-HCl, 50 mM, pH 7.7). To the reporter background wells was added 5 µL Tris-HCl and 5 µL 1:1 Tris-HCl:DMSO. Similarly, to the control wells was added 5 µL 1:1 Tris-HCl:DMSO. To the test wells was added 2.5 µL Tris-HCl and 2.5 µL of a 500 µM solution of the compound of interest in DMSO. This resulted in a final concentration of 25 µM of the compound in the 96-well plate. Immediately prior to running the assay on the Synergy 4 Plate Reader, 5 µL purified 20S proteasome (90 nM in Tris-HCl) was added to the control and test wells.

The assay was performed using the Synergy 4 plate reader as described for the general screening kinetic assay procedure.

Dose Response Assay for 1, 2, and 3

The ability of compounds 1, 2, and 3 to stimulate the CT-L activity of the 20S proteasome was tested in a dose-response manner at the following concentrations of compound in triplicate: 400, 200, 100, 50, 25, 12.5, 6.25, 3.125, 1.5625, 0.78125 and 0 µM.

To each well was added 40 µL 20 µM reporter (in Tris-HCl) and 2.5 µL Tris-HCl. To the reporter background wells was added 5 µL Tris-HCl and 5 µL 1:1 Tris-HCl:DMSO. Similarly, to the control wells was added 5 µL 1:1 Tris-HCl:DMSO. To the test wells was added 2.5 µL Tris-HCl. Solutions of 1 were prepared in DMSO at the following concentrations, corresponding to the final concentrations of 1 mentioned above: 8000, 4000, 2000, 1000, 500, 250, 125, 62.5, 31.25, and 15.625 µM 1, respectively. From these solutions, 2.5 µL was added to the appropriate test wells in the 96-well plate. Immediately prior to reading the plate with the Synergy 4 plate reader, 5 μL purified 20S proteasome (90 nM in Tris-HCl) was added to the wells at a final concentration of 9 nM per well.

The assay was performed using the Synergy 4 plate reader as described for the general screening kinetic assay procedure.

The above procedure was also performed for 2 and 3.

Screening 1, 2, and 3 with 26S Proteasome

Compounds 1, 2, and 3 were screened with the 26S proteasome in triplicate using the CT-L FRET reporter.

To each well was added 40 μL 20 μM CT-L FRET reporter (in Tris-HCl, 50 mM, pH 7.7). To the reporter background wells was added 5 μL Tris-HCl and 5 μL 1:1 Tris-HCl:DMSO. Similarly, to the control wells was added 5 μL 1:1 Tris-HCl:DMSO. To the test wells was added 2.5 μL Tris-HCl and 2.5 μL of a 500 μM solution of the compound of interest in DMSO. This resulted in a final concentration of 25 μM of the compound in the 96-well plate. Immediately prior to running the assay on the Synergy 4 Plate Reader, 5 μL purified 26S proteasome (62.5 μg/mL in Tris-HCl) was added to the control and test wells.

The assay was performed using the Synergy 4 plate reader as described for the general screening kinetic assay procedure.

Screening 1, 2, and 3 with the Immunoproteasome

Compounds 1, 2, and 3 were screened with the immunoproteasome in triplicate using the CT-L FRET reporter.

To each well was added 40 μL 20 μM CT-L FRET reporter (in Tris-HCl, 50 mM, pH 7.7). To the reporter background wells was added 5 μL Tris-HCl and 5 μL 1:1 Tris-HCl:DMSO. Similarly, to the control wells was added 5 μL 1:1 Tris-HCl:DMSO. To the test wells was added 2.5 μL Tris-HCl and 2.5 μL of a 500 μM solution of the compound of interest in DMSO. This resulted in a final concentration of 25 μM of the compound in the 96-well plate. Immediately prior to running the assay on the Synergy 4 Plate Reader, 5 μL purified 26S proteasome (62.5 μg/mL in Tris-HCl) was added to the control and test wells.

The assay was performed using the Synergy 4 plate reader as described for the general screening kinetic assay procedure.

Kinetic Assay Data Analysis

All of the data obtained from the Synergy 4 plate reader for the kinetic screening assay was processed using GraphPad Prism. With the exception of the data obtained from screening the Natural Product Library, all of the raw data obtained was directly analyzed with GraphPad Prism. For the Natural Product Library, the raw data obtained from the background wells was subtracted from the raw data obtained from the test wells. The resulting data was considered normalized; the raw data from the control wells and the normalized data from the test compounds were analyzed using the GraphPad Prism program.

For all of the assays, the fluorescent data was plotted against time in minutes. The linearized slope produced by these plots was considered the rate of hydrolysis of the fluorescent reporters by the 20S proteasome.

GraphPad Prism was used to produce the dose-response plots of the CT-L FRET reporter (FIG. 10), SDS (FIG. 11a), 1, 2, and 3.

APPENDIX

High-Throughput Screen Calculations

The data obtained from testing the effects of the positive control (AM-404) and the negative control (fenofibrate) on the 20S CP using the CT-L FRET reporter were used to determine the efficiency of using the CT-L FRET reporter in a HTS campaign. The following equations were used:

$$\text{Signal-to-noise ratio } (S/N): \frac{S}{N} = \frac{\text{mean signal} - \text{mean background}}{\text{standard deviation of background}}$$

$$\text{Signal-to-background ratio } (S/B): \frac{S}{B} = \frac{\text{mean signal}}{\text{mean background}}$$

$$\text{Coefficient of variation } (\% \ CV): \% \ CV = 100 * \frac{\text{standard deviation}}{\text{mean signal}}$$

$$Z'\text{-factor } (Z'): Z' = 1 - \frac{3(SD \ pos \ \text{control} - SD \ neg \ \text{control})}{|\text{mean } pos \ \text{control} - \text{mean } neg \ \text{control}|}$$

In conclusion, we report here a new set of FRET reporters to screen for 20S CP stimulating molecules. We show that these reporters are much more sensitive to stimulation than the commonly used three to four amino acid-coumarin reporters but still retain the high throughput nature of a fluorescent assay. With this added sensitivity, we for the first time report here a small molecule that elicits only stimulation of the chymotrypsin-like activity of the 20S CP. We also discovered two other molecules that present as 20S CP gate openers. Molecules that stimulate the activity of the 20S CP through either of these mechanisms are of great interest to evaluate the validity of this therapeutic strategy for treating protein-accumulation diseases. Stimulation of the 20S CP has been proposed as a potential therapy for Parkinson's disease, Alzheimer's disease, and to limit some negative effects associated with aging.[37] The same mechanism of 20S CP stimulation may not be applicable to all of these disease states, and with the molecules we have in hand, we can begin to elucidate which mechanism is applicable for which disease type. The scaffolds we discovered can be modified to generate more potent and selective 20S CP stimulators to begin to evaluate the therapeutic potential of this mechanism in 3-D cell cultures of neurons, senescent cell models, and eventually animal models of these diseases. Finally, we hope these new FRET reporters are used by others to continue to discover more 20S CP stimulation molecules to aid in the further exploration of this potential therapeutic mechanism.

REFERENCES (1) Bhattacharyya, S.; Yu, H.; Mim, C.; Matouschek, A. Nat. Rev. Mol. Cell Biol. 2014, 15, 122-133.

(2) Huang, X.; Luan, B.; Wu, J.; Shi, Y. Nat. Struct. Mol. Biol. 2016, 23 (9), 778-785.
(3) Rechsteiner, M.; Hill, C. P. Trends Cell Biol. 2005, 15 (1), 27-33.
(4) Goldberg, A. L. J. Cell Biol. 2012, 199 (4), 583-588.
(5) Trader, D. J.; Simanski, S.; Kodadek, T. J. Am. Chem. Soc. 2015, 137 (19), 6312-6319.
(6) Li, J.; Yakushi, T.; Parlati, F.; Mackinnon, A. L.; Perez, C.; Ma, Y.; Carter, K. P.; Colayco, S.; Magnuson, G.; Brown, B.; Nguyen, K.; Vasile, S.; Suyama, E.; Smith, L. H.; Sergienko, E.; Pinkerton, A. B.; Chung, T. D. Y.; Palmer, A. E.; Pass, I.; Hess, S.; Cohen, S. M.; Deshaies, R. J. Nat. Chem. Biol. 2017, 13 (5), 486-493.
(7) Wang, X.; Yen, J.; Kaiser, P.; Huang, L. Sci. Signal. 2010, 3 (151), ra88.
(8) Ben-Nissan, G.; Sharon, M. Biomolecules 2014, 4 (3), 862-884.
(9) Husom, A. D.; Peters, E. A.; Kolling, E. A.; Fugere, N. A.; Thompson, L. V.; Ferrington, D. A. Arch. Biochem. Biophys. 2004, 421 (1), 67-76.
(10) McNaught, K. S.; Jenner, P. Neurosci. Lett. 2001, 297 (3), 191-194.
(11) Chondrogianni, N.; Sakellari, M.; Lefaki, M.; Papaevgeniou, N.; Gonos, E. S. Free Radic. Biol. Med. 2014, 71, 303-320.
(12) Kapetanou, M.; Chondrogianni, N.; Petrakis, S.; Koliakos, G.; Gonos, E. S. Free Radic. Biol. Med. 2017, 103, 226-235.
(13) Smith, D. M.; Kafri, G.; Cheng, Y.; Ng, D.; Walz, T.; Goldberg, A. L. Mol. Cell 2005, 20 (5), 687-698.
(14) Latham, M. P.; Sekhar, A.; Kay, L. E. Proc. Natl. Acad. Sci. 2014, 111 (15), 5532-5537.
(15) Tan, X.; Osmulski, P. A.; Gaczynska, M. Curr. Med. Chem. 2006, 13 (2), 155-165.
(16) Dal Vechio, F. H.; Cerqueira, F.; Augusto, O.; Lopes, R.; Demasi, M. Free Radic. Biol. Med. 2014, 67, 304-313.
(17) Smith, D. M.; Chang, S.-C.; Park, S.; Finley, D.; Cheng, Y.; Goldberg, A. L. Mol. Cell 2007, 27 (5), 731-744.
(18) Kisselev, A. F. J. Biol. Chem. 2002, 277 (25), 22260-22270.
(19) Katsiki, M.; Chondrogianni, N.; Chinou, I.; Rivett, A. J.; Gonos, E. S. Rejuvenation Res. 2007, 10 (2), 157-172.
(20) Huang, L.; Ho, P.; Chen, C.-H. FEBS Lett. 2007, 581 (25), 4955-4959.
(21) Watanabe, N.; Yamada, S. Plant Cell Physiol. 1996, 37 (2), 147-151.
(22) Priestman, M. A.; Wang, Q.; Jernigan, F. E.; Chowdhury, R.; Schmidt, M.; Lawrence, D. S. ACS Chem. Biol. 2015, 10 (2), 433-440.
(23) Leestemaker, Y.; de Jong, A.; Witting, K. F.; Penning, R.; Schuurman, K.; Rodenko, B.; Zaal, E. A.; van de Kooij, B.; Laufer, S.; Heck, A. J. R.; Borst, J.; Scheper, W.; Berkers, C. R.; Ovaa, H. Cell Chem. Biol. 2017, 24 (6), 725-736.e7.
(24) Liggett, A.; Crawford, L. J.; Walker, B.; Morris, T. C. M.; Irvine, A. E. Leuk. Res. 2010, 34 (11), 1403-1409.
(25) Urru, S. A. M.; Veglianese, P.; De Luigi, A.; Fumagalli, E.; Erba, E.; Gonella Diaza, R.; Carra, A.; Davoli, E.; Borsello, T.; Forloni, G.; Pengo, N.; Monzani, E.; Cascio, P.; Cenci, S.; Sitia, R.; Salmona, M. J. Med. Chem. 2010, 53 (20), 7452-7460.
(26) Keita, M.; Kaffy, J.; Troufflard, C.; Morvan, E.; Crousse, B.; Ongeri, S. Org. Biomol. Chem. 2014, 12 (26), 4576-4581.
(27) de Bruin, G.; Xin, B.-T.; Florea, B. I.; Overkleeft, H. S. J. Am. Chem. Soc. 2016, 138 (31), 9874-9880.
(28) Jin, S.; Ellis, E.; Veetil, J. V.; Yao, H.; Ye, K. Biotechnol. Prog. 2011, 27 (4), 1107-1114.
(29) Tanaka, K.; Yoshimura, T.; Ichihara, A. J. Biochem. (Tokyo) 1989, 106 (3), 495-500.
(30) Trader, D.; Simanski, S.; Kodadek, T. Biochim Biophys Acta 2017, 1861, 892-899.
(31) Ferrington, D. A.; Gregerson, D. S. In Progress in Molecular Biology and Translational Science; Elsevier, 2012; Vol. 109, pp 75-112.
(32) Lee, B.-H.; Lee, M. J.; Park, S.; Oh, D.-C.; Elsasser, S.; Chen, P.-C.; Gartner, C.; Dimova, N.; Hanna, J.; Gygi, S. P.; Wilson, S. M.; King, R. W.; Finley, D. Nature 2010, 467 (7312), 179-184.
(33) Chen, L.; Brewer, M. D.; Guo, L.; Wang, R.; Jiang, P.; Yang, X. Cell Rep. 2017, 18 (13), 3143-3154.
(34) Toth, G.; Gardai, S. J.; Zago, W.; Bertoncini, C. W.; Cremades, N.; Roy, S. L.; Tambe, M. A.; Rochet, J.-C.; Galvagnion, C.; Skibinski, G.; Finkbeiner, S.; Bova, M.; Regnstrom, K.; Chiou, S.-S.; Johnston, J.; Callaway, K.; Anderson, J. P.; Jobling, M. F.; Buell, A. K.; Yednock, T. A.; Knowles, T. P. J.; Vendruscolo, M.; Christodoulou, J.; Dobson, C. M.; Schenk, D.; McConlogue, L. PloS One 2014, 9 (2), e87133.
(35) Liu, C.-W. Science 2003, 299 (5605), 408-411.
(36) Singla, P.; Luxami, V.; Paul, K. Eur. J. Med. Chem. 2015, 102, 39-57.
(37) Huang, Q.; Figueiredo-Pereira, M. E. Apoptosis 2010, 15 (11), 1292-1311.

The invention claimed is:

1. A method to identify a CP 20S stimulator as a therapeutic or for a diagnostic method through accelerating protein degradation, comprising:
    chemically constructing a fluorescence reporter with the following structure:

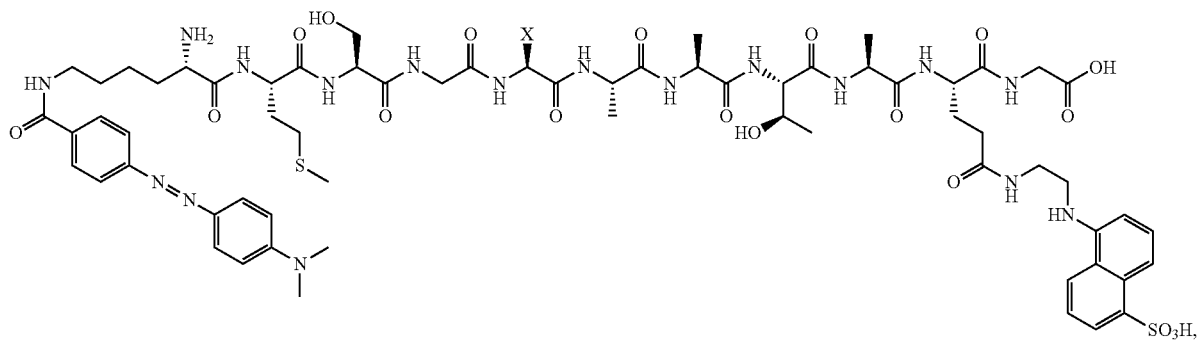

CT-L FRET: X = Phe
T-L FRET: X = Arg
CP-L FRET: X = Asp wherein CT-L FRET, X=Phe (SEQ ID NO: 1); T-L FRET, X=Arg (SEQ ID NO: 2); and CP-L FRET, X=Asp (SEQ ID NO: 3);
    individually pairing the fluorescence reporter with each candidate compound in a library as said CP 20S stimulator and supplying CP 20S to the pair to obtain the fluorescence reporter hydrolysis reading;
    providing a positive control with the fluorescence reporter and CP 20S to obtain a reference fluorescence reporter hydrolysis reading; and
    affording said CP 20S stimulator as a therapeutic or for a diagnostic method, which is the candidate compound that matches or surpasses the reference fluorescence reporter hydrolysis reading.

2. The method according to claim 1, wherein the positive control is sodium dodecyl sulfate (SDS) or AM-404.

3. The method according to claim 1, wherein the fluorescence reporter hydrolysis reading is expressed by the rate of hydrolysis in relative fluorescence units (RFU) per minute ($\Delta$RFU/Min).

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Artificial sequence
<220> FEATURE:
<223> OTHER INFORMATION: CT-L FRET, X=Phe
<220> FEATURE:
<221> NAME/KEY: Lys(Y1)
<222> LOCATION: (1)..(1)
<223> OTHER INFORMATION: Lys sidechain modified
<220> FEATURE:
<221> NAME/KEY: Glu(Y2)
<222> LOCATION: (10)..(10)
<223> OTHER INFORMATION: Glu sidechain modified
```

```
<400> SEQUENCE: 1

Lys Met Ser Gly Phe Ala Ala Thr Ala Glu Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: T-L FRET, X=Arg
<220> FEATURE:
<221> NAME/KEY: Lys(Y1)
<222> LOCATION: (1)..(1)
<223> OTHER INFORMATION: Lys sidechain modified
<220> FEATURE:
<221> NAME/KEY: Glu(Y2)
<222> LOCATION: (10)..(10)
<223> OTHER INFORMATION: Glu sidechain modified

<400> SEQUENCE: 2

Lys Met Ser Gly Arg Ala Ala Thr Ala Glu Gly
1               5                   10

<210> SEQ ID NO 3
<211> LENGTH: 11
<212> TYPE: PRT
<213> ORGANISM: Artificial Sequence
<220> FEATURE:
<223> OTHER INFORMATION: CP-L FRET, X=Asp
<220> FEATURE:
<221> NAME/KEY: Lys(Y1)
<222> LOCATION: (1)..(1)
<223> OTHER INFORMATION: Lys sidechain modified
<220> FEATURE:
<221> NAME/KEY: Glu(Y2)
<222> LOCATION: (10)..(10)
<223> OTHER INFORMATION: Glu sidechain modified

<400> SEQUENCE: 3

Lys Met Ser Gly Asp Ala Ala Thr Ala Glu Gly
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Suc-LLVY-AMC
<220> FEATURE:
<221> NAME/KEY: Leu
<222> LOCATION: (1)..(1)
<223> OTHER INFORMATION: alpha amino modified
<220> FEATURE:
<221> NAME/KEY: Tyr
<222> LOCATION: (4)..(4)
<223> OTHER INFORMATION: C-terminal end modified

<400> SEQUENCE: 4

Leu Leu Val Tyr
1
```